(12) United States Patent
Raupp

(10) Patent No.: US 8,429,989 B2
(45) Date of Patent: Apr. 30, 2013

(54) MODULAR APPARATUS AND METHOD FOR ROTATING GLASS CONTAINERS AND THE LIKE

(75) Inventor: Henry F. Raupp, Freeville, NY (US)

(73) Assignee: Emhart Glass S.A., Cham (CH)

( * ) Notice: Subject to any disclaimer, the term of this patent is extended or adjusted under 35 U.S.C. 154(b) by 789 days.

(21) Appl. No.: 12/253,951

(22) Filed: Oct. 18, 2008

(65) Prior Publication Data

US 2010/0095790 A1  Apr. 22, 2010

(51) Int. Cl.
*G01M 99/00* (2011.01)
(52) U.S. Cl.
USPC .......................................................... 73/865.8
(58) Field of Classification Search .................. 73/865.8
See application file for complete search history.

(56) References Cited

U.S. PATENT DOCUMENTS

| | | | |
|---|---|---|---|
| 3,262,561 A | 7/1966 | Sorbie | |
| 3,348,049 A | 10/1967 | Stacey | |
| 3,410,388 A * | 11/1968 | Horn et al. | 209/523 |
| 3,426,884 A | 2/1969 | Donner | |
| 3,460,669 A | 8/1969 | Johnson | |
| 3,557,950 A | 1/1971 | Powers | |
| 3,684,089 A | 8/1972 | McMeekin | |
| 3,690,456 A | 9/1972 | Powers, Jr. | |
| 3,735,855 A | 5/1973 | Johnson et al. | |
| 3,848,742 A | 11/1974 | Krenmayr | |
| 3,938,653 A | 2/1976 | Senger | |
| 3,957,154 A | 5/1976 | Shiba | |
| 3,991,883 A | 11/1976 | Hobler et al. | |
| 4,021,122 A | 5/1977 | Krenmayr | |
| 4,323,158 A | 4/1982 | Wheaton, III et al. | |
| 4,650,326 A | 3/1987 | Negamine et al. | |
| 4,653,628 A | 3/1987 | Claypool et al. | |
| 4,786,801 A | 11/1988 | Shay | |
| 4,915,237 A | 4/1990 | Chang et al. | |
| 4,967,070 A | 10/1990 | Ringlien et al. | |
| 5,028,769 A | 7/1991 | Claypool et al. | |
| 5,405,015 A | 4/1995 | Bhatia et al. | |
| 5,608,516 A | 3/1997 | Emery | |
| 5,719,679 A | 2/1998 | Shimizu et al. | |
| 5,823,317 A | 10/1998 | Bankuty et al. | |
| 5,895,911 A | 4/1999 | Giometti et al. | |
| 6,012,344 A | 1/2000 | Halbo | |
| 6,172,355 B1 * | 1/2001 | Gast et al. | 250/223 B |

FOREIGN PATENT DOCUMENTS

GB  1155976  6/1969

* cited by examiner

*Primary Examiner* — Hezron E Williams
*Assistant Examiner* — Nashmiya Fayyaz
(74) *Attorney, Agent, or Firm* — Reinhart Boerner Van Deuren s.c.

(57) ABSTRACT

An apparatus and method for rotating glass containers and like wares for purposes of inspection is disclosed that uses a compact, modular apparatus which has a drive system that automatically accelerates the wares to full rotation speed while applying only the amount of contact force to the wares that is required to rotate them. The apparatus of the present invention is compact and thus consumes minimal volume in the area near the glass container being rotated. The apparatus for rotating glass containers of the present invention has an outstanding ability to move quickly into contact with a glass container and accelerate it to its full speed without damaging it or being damaged by it, and presents a low degree of impact to glass containers.

20 Claims, 15 Drawing Sheets

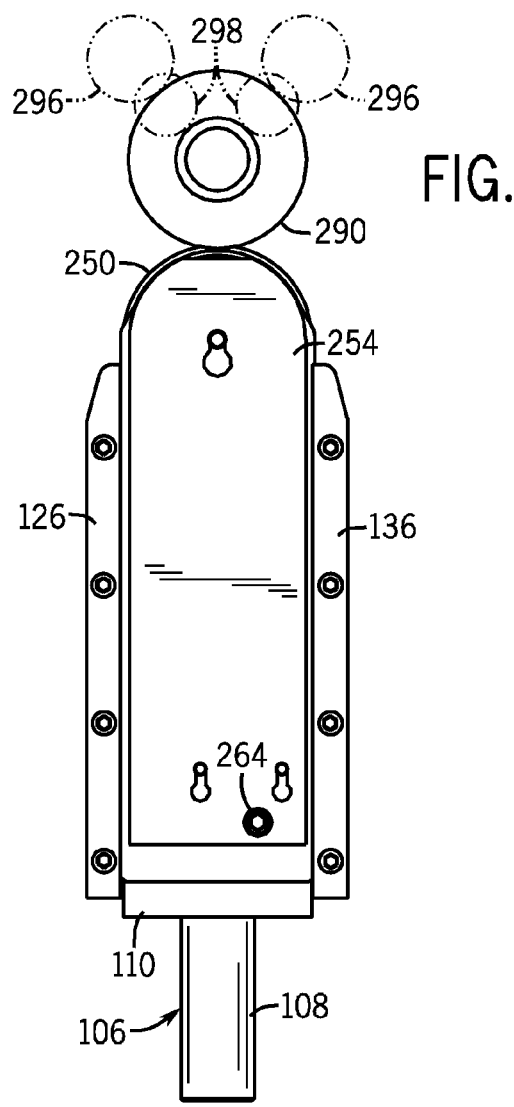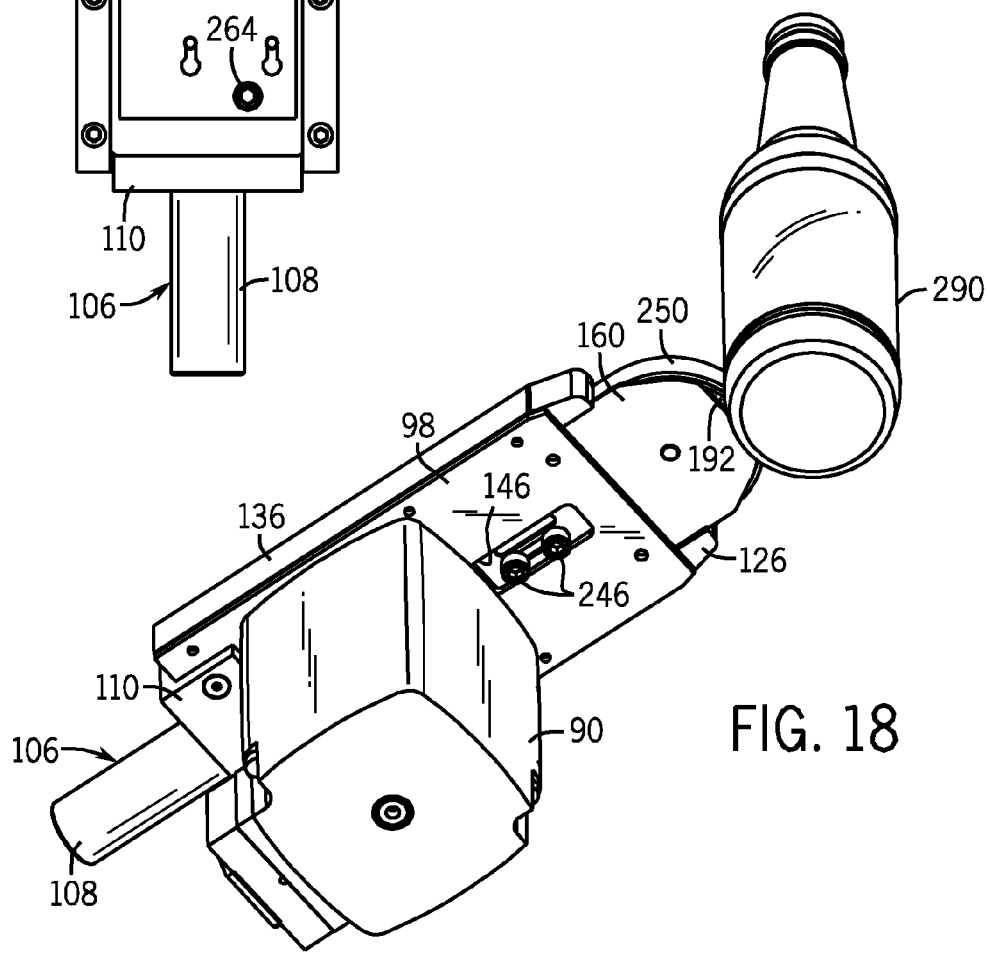

MODULAR APPARATUS AND METHOD FOR ROTATING GLASS CONTAINERS AND THE LIKE

BACKGROUND OF THE INVENTION

Field of the Invention

The present invention relates generally to apparatus and methods for rotating glass containers and like wares for purposes of inspection, and more particularly to an improved compact, modular apparatus and method for rotating such wares that more quickly accelerates them to full rotation speed through a novel drive system that automatically applies only the amount of contact force to the wares that is required to rotate them.

Glass containers are made in a manufacturing process that has three parts, namely the batch house, the hot end, and the cold end. The batch house is where the raw materials for glass (which may typically include sand, soda ash, limestone, cullet (crushed, recycled glass), and other raw materials) are prepared and mixed into batches. The hot end begins with a furnace, in which the batched materials are melted into molten glass, and from which a stream of molten glass flows.

The molten glass is cut into cylinders of glass called gobs, which fall by gravity into blank molds. In the blank molds, a pre-container referred to as a parison is formed, either by using a metal plunger to push the glass into the blank mold, or by blowing the glass from below into the blank mold. The parison is inverted and transferred to a mold, where the parison is blown out into the shape of the container. The hot end also includes an annealing process which prevents the containers from having weakened glass caused by stresses caused by uneven cooling. The annealing process is used to achieve even cooling, using an annealing oven or Lehr to heat the containers, and then slowly cool them over a twenty to sixty minute period.

The role of the cold end of the glass container manufacturing process is inspection of the containers to ensure that they are of acceptable quality. All glass containers are inspected by automated machines after manufacturing for a variety of faults, typically including small cracks in the glass referred to as checks, foreign inclusions referred to as stones, bubbles in the glass referred to as blisters, and excessively thin walls. Many of these inspections are carried out by rotating the glass containers in order to check the glass containers on all sides thereof, or at least at a plurality of angularly spaced apart locations on the glass containers. In addition, many glass containers include a "heel code," which is a mold code on the heel of each glass container (the rounded portion where the horizontal plane of the base transitions into a vertical cylinder, also known as the insweep), which identify the particular mold in which the glass container was blow molded. See, for example, U.S. Pat. No. 5,028,769, to Claypool et al., which is assigned to the assignee of the present invention, and which patent is hereby incorporated herein by reference.

Since these inspections are performed as part of a large scale manufacturing process, those skilled in the art will appreciate that it must be performed at high speed, for example at an inspection rate of approximately 400 glass containers per minute. Thus, in the space of approximately 150 milliseconds, a glass container must have been brought into the inspection station, rotated through approximately one and one-half rotations, and taken out of the inspection station as another glass container is brought into the inspection station.

Typically, an inspection station is located in either an indexing starwheel conveyer having upper and lower spaced wheels with cutouts for receiving the glass containers (as shown, for example, in U.S. Pat. No. 3,957,154, to Shiba), or at a straight conveyer inspection area having apparatus for rotating glass containers located at one or more desired positions on a straight conveyer defining a container path or track (as shown, for example, in U.S. Pat. No. 5,608,516, to Emery). In either case, the inspection station will have a pair of rollers that support a glass container near its top on one side of the glass container and a second pair of rollers that support the glass container nearer its bottom on the same side of the glass container. A drive roller contacts the glass container on the side opposite its support by the two pairs of rollers, and is driven by a drive mechanism to cause the glass container to rotate between the drive roller and the two pairs of rollers respectively supporting the top and bottom of the glass container.

The drive roller causes the glass container to rotate between the drive roller and the two pairs of rollers, and various inspections may be made while the glass container is rotating. Such inspections may be optical or mechanical in nature, and are typically performed at a plurality of angular increments as the glass container is rotated. The drive roller typically operates continuously (whether or not it is in contact with glass containers), and is located adjacent a pathway traversed by glass containers in a location opposite two pairs of rollers.

Two different types of drive mechanism have been used in the industry to operate and position a drive roller to rotate glass containers in inspection stations. The first such drive mechanism is an apparatus wherein the entire apparatus is pivotally mounted about a horizontal axis so that the entire mechanism pivots, with the drive roller pivoting in a vertical plane toward and away from the glass container to be driven, and with the drive roller being spring biased toward the glass container (shown, for example, in the Shiba patent). This drive apparatus is very hard on glass containers in a high speed (400 containers per minute) line, "hammering" the containers due to the high mass of the drive assembly and damaging them as well as having significant reliability issues.

The second such drive mechanism is an apparatus that is mounted in an offset manner wherein the part of the apparatus including the drive roller is pivotally mounted about a vertical axis so that the drive roller pivots in a horizontal plane toward and away from the glass container to be driven, with the drive roller being spring biased toward the glass container (shown, for example, in the Emery patent). This drive apparatus has less moving mass and thus is not as hard on glass containers, but it is more expensive to manufacture, it requires more space near the path of the glass containers, and it also has significant reliability issues.

It is accordingly a primary objective of the present invention that it provide an improved apparatus for rotating glass containers that is highly compact to enable it to consume minimal volume in the area near the glass container being rotated to thereby allow the maximum amount of room possible for inspection apparatus. It is another primary objective of the present invention that despite its compact size it have the ability to supply sufficient torque to the glass container to accelerate it rapidly to minimize the time required to inspect each glass container. It is a related objective of the present invention that it present a highly compliant drive surface and that it also provide an increased capacity to quickly "nip" the outer wall of the glass container to rapidly overcome its inertia and spin it up to speed.

It is yet another primary objective of the present invention that it present a low degree of impact to glass containers, and that it have an outstanding ability to move quickly into contact with the glass container without damaging it or being damaged by it. It is a further objective of the present invention that it be capable of imparting a downwardly acting force to the glass container, which is otherwise unrestrained in the vertical direction as it is being rotated at high speed. It is still another objective of the present invention that it be of robust mechanical design and of high reliability to avoid any loss of production occasioned by it failing.

The apparatus for rotating glass containers of the present invention must also be of construction which is both durable and long lasting and have construction characteristics that allow it to be serviced quickly, although it should also require only relatively infrequent maintenance to be provided by the user throughout its operating lifetime. In order to enhance the market appeal of the apparatus for rotating glass containers of the present invention, it should also be of inexpensive construction to thereby afford it the broadest possible market. Finally, it is also an objective that all of the aforesaid advantages and objectives of the apparatus for rotating glass containers and method of the present invention be achieved without incurring any substantial relative disadvantage.

SUMMARY OF THE INVENTION

The disadvantages and limitations of the background art discussed above are overcome by the present invention. With this invention, a highly compact apparatus for rotating glass containers is provided which has two principal components, namely a base assembly that includes an electric motor and a carriage assembly that is installed in the base assembly and which rotates a glass container. The apparatus for rotating glass containers of the present invention uses a ware rotate belt rotating about a resilient ware rotate wheel to rotate the glass container. This "belt around a wheel" design allows the apparatus to be very thin and narrow, with its size adjacent the glass container being little larger than the size of the ware rotate wheel itself.

The base assembly has a motor that drives a drive belt pulley and also includes one idler pulley. The base assembly also includes apparatus for supporting the carriage assembly therein in a manner allowing it to slide in a linear direction toward (in a distal direction) and away from (in a proximal direction) the glass container. The carriage assembly is biased in a distal direction by springs located between the carriage assembly and the base assembly. The bias on the springs is adjustable to vary the force that will be applied to a glass container engaged by the apparatus for rotating glass containers.

The carriage assembly includes idler pulleys mounted therein, as well as a tensioner assembly carrying an idler pulley the position of which may be adjusted to adjust the tension on the ware rotate belt. The ware rotate belt is a toothed belt having a longitudinally extending groove cut into the teeth of the toothed belt in the centerline thereof. The drive belt pulley in the base assembly and the ware rotate wheel as well as the two idler pulleys in the carriage assembly are toothed and have an annular rib extending outwardly of the teeth at the centerline thereof. This groove in the ware rotate belt engages the rib in the drive belt pulley, the ware rotate wheel, and the two idler pulleys, which enhances the ability of the ware rotate belt to sustain a load across its axis of rotation (as well as to decrease the height of the apparatus for rotating glass containers where it is close to them.

This approach allows the ware rotate belt, the ware rotate wheel, and the bearings for the ware rotate wheel to all have a common centerline. This planar design provides both an increased level of reliability and a great reduction is size, particularly in the area near the glass container being inspected. The space near the glass container being inspected is the space that is most valuable for the placement of glass container inspection sensors, and the design of the apparatus for rotating glass containers of the present invention maximizes the area around the glass container that is available for inspection sensors.

In addition, the design of the apparatus for rotating glass containers of the present invention has a greatly reduced impact on the glass containers it rotates. First, the spring biasing is the only force that is exerted on a glass container as it is rotating. When a glass container is in the process of beginning to rotate, the configuration of the ware rotate belt drive path will result in increased tension in a portion of the ware rotate belt as a glass container is being accelerated up to its full rotation speed. This increased tension serves to move the carriage assembly toward the glass container, applying additional pressure to the glass container to improve the grip exerted by the ware rotate belt on the glass container while it is being accelerated. Once the glass container is rotating at its full speed, the increased tension in the ware rotate belt disappears and the carriage assembly retracts, with the additional pressure exerted on the glass container also disappearing.

It may therefore be seen that the present invention teaches an apparatus for rotating glass containers of the present invention is highly compact, enabling it to consume minimal volume in the area near the glass container being rotated to thereby allow the maximum amount of room possible for inspection apparatus. Despite the compact size of the apparatus for rotating glass containers of the present invention, it has the ability to supply sufficient torque to the glass container to accelerate it rapidly to minimize the time required to inspect each glass container. The apparatus for rotating glass containers of the present invention presents a highly compliant drive surface and also provides an increased capacity to quickly "nip" the outer wall of the glass container to rapidly overcome its inertia and spin it up to speed.

The apparatus for rotating glass containers of the present invention presents a low degree of impact to glass containers, and has an outstanding ability to move quickly into contact with the glass container without damaging it or being damaged by it. The apparatus for rotating glass containers of the present invention is also capable of imparting a downwardly acting force to the glass container, thereby acting to restrain it downwardly as it is being rotated at high speed. The apparatus for rotating glass containers of the present invention is of robust mechanical design and of high reliability to avoid any loss of production occasioned by it failing.

The apparatus for rotating glass containers of the present invention is of a construction which is both durable and long lasting and has construction characteristics that allow it to be serviced quickly, and it will require only relatively infrequent maintenance to be provided by the user throughout its operating lifetime. The apparatus for rotating glass containers of the present invention is also of inexpensive construction to enhance its market appeal and to thereby afford it the broadest possible market. Finally, all of the aforesaid advantages and objectives of the apparatus for rotating glass containers and method of the present invention are achieved without incurring any substantial relative disadvantage.

DESCRIPTION OF THE DRAWINGS

These and other advantages of the present invention are best understood with reference to the drawings, in which:

FIG. 17 is a top plan view of the fully assembled apparatus for rotating glass containers of the present invention in position to rotate a glass container;

FIG. 18 is an isometric view similar to that of FIG. 17, but showing the bottom of the fully assembled apparatus for rotating glass containers;

DETAILED DESCRIPTION OF THE EXEMPLARY EMBODIMENTS

Figure 1:
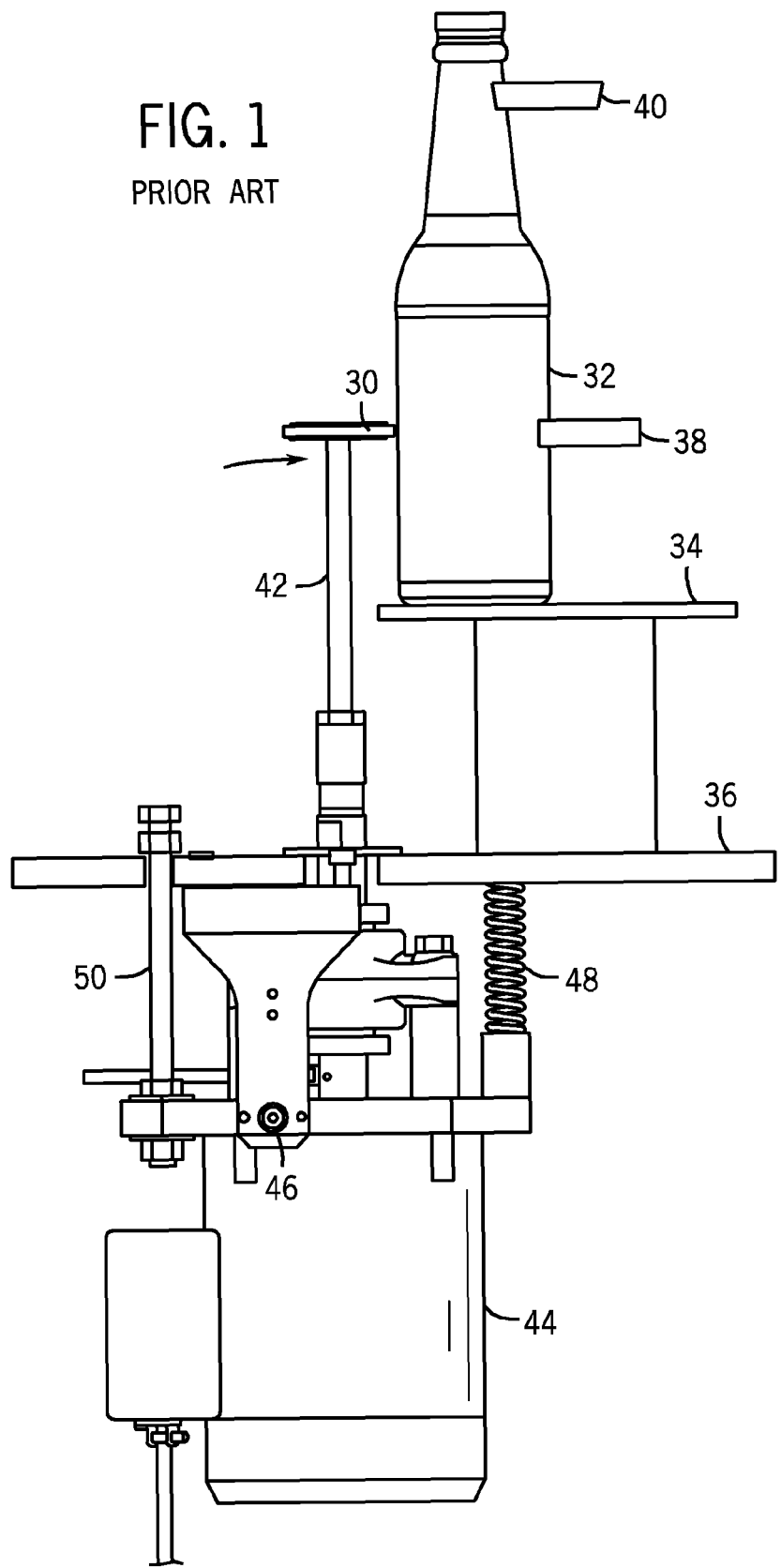
FIG. 1 is a side view of a first presently known apparatus for rotating glass containers.

Prior to discussing an exemplary embodiment of the apparatus for rotating glass containers and method of the present invention, it is helpful to briefly discuss previously known devices that are used for operating and positioning a drive roller to rotate a glass container in an inspection station. The first such drive mechanism is shown in FIG. 1, and is an apparatus that is pivotally mounted about a horizontal axis so that the entire mechanism pivots, with a drive roller 30 being spring biased to pivot in a vertical plane toward a glass container 32 to be rotated. The glass container 32 is supported on a deadplate 34 that is located above a top plate 36, with the glass container 32 being supported for rotation on one side thereof near its bottom by a pair of rollers 38 and near its top by a second pair of rollers 40.

The drive roller 30 is mounted on a shaft 42 that is driven by a motor 44 mounted below the top plate 36 on a pivot mechanism 46 that allows the motor 44 to pivot about a horizontal axis in a manner causing the drive roller 30 to move toward and away from the glass container 32. A spring 48 is used to bias the motor 44 to pivot in a manner urging the drive roller 30 toward the glass container 32. A limiting mechanism 50 is used to limit the biased pivoting of the motor 44 to thereby also limit the distance that the drive roller 30 can move toward the glass container 32 to prevent damage from occurring to the glass container 32. As mentioned above, the drive apparatus shown in FIG. 1 is very hard on glass containers 32 in a high speed inspection line, "hammering" the glass containers 32 due to the high mass of the drive assembly and potentially damaging them.

Figure 2:
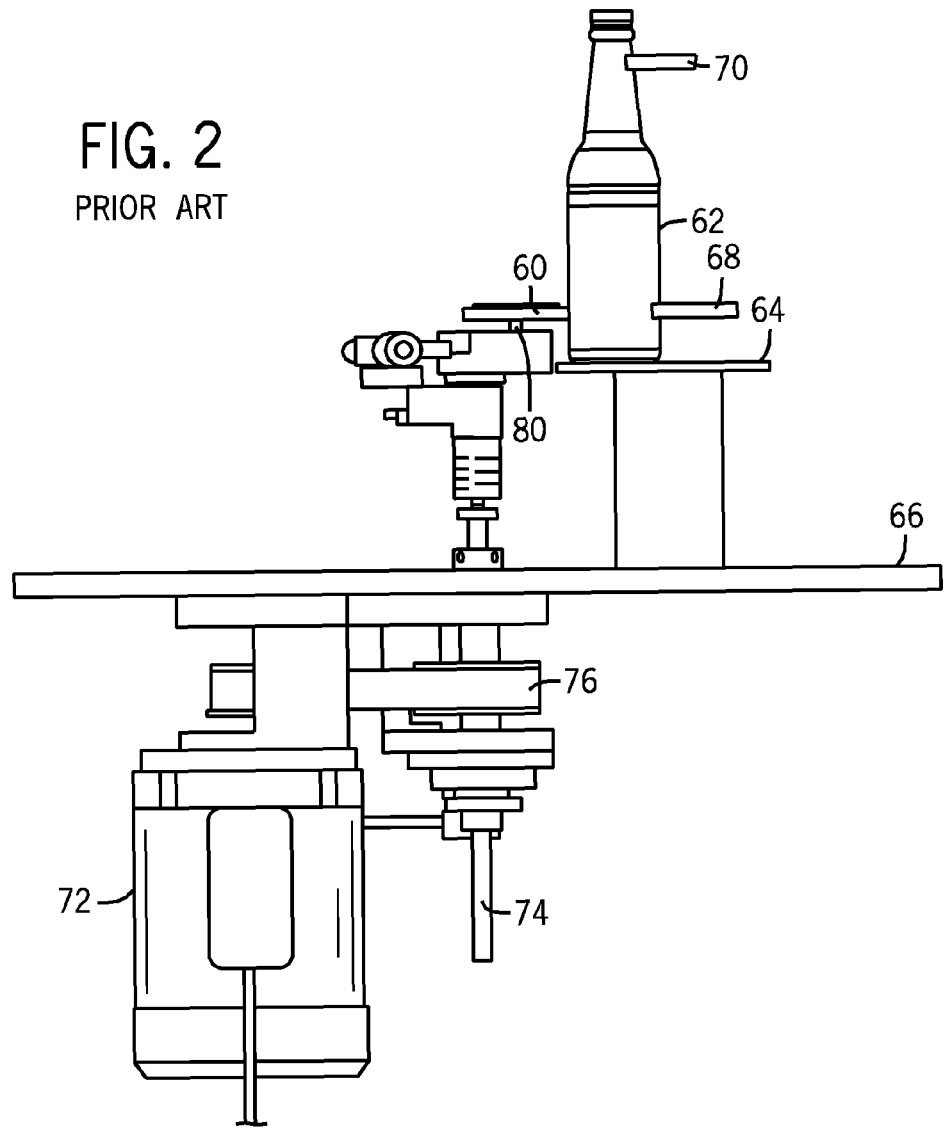
FIG. 2 is a side view of a second presently known apparatus for rotating glass containers.
Figure 3:
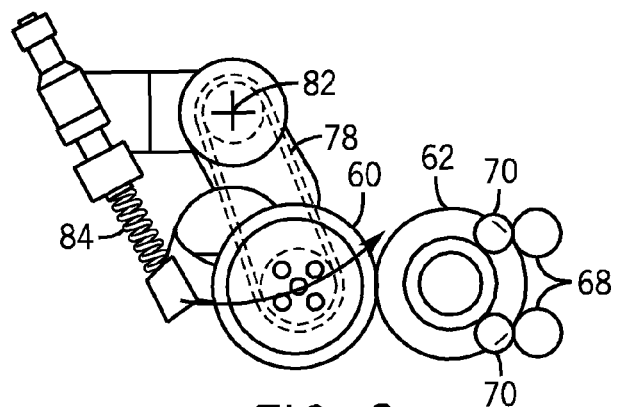
FIG. 3 is a top plan view of the second presently known apparatus for rotating glass containers illustrated in FIG. 2.

The second previously known drive mechanism for operating and positioning a drive roller to rotate a glass container in an inspection station is shown in FIGS. 2 and 3, and is an apparatus that has a drive roller 60 that is pivotally mounted about a vertical axis so that the drive roller 60 is spring biased to pivot in a horizontal plane toward the glass container 62 to be driven. The glass container 62 is supported on a deadplate 64 that is located above a top plate 66, with the glass container 62 being supported for rotation on one side thereof near its bottom by a pair of rollers 68 and near its top by a second pair of rollers 70.

A motor 72 is mounted below the top plate 66 and drives a shaft 74 with a drive belt 76. The shaft 74 extends upwardly through the top plate 66 and drives a second drive belt 78 that drives a shaft 80 that the drive roller 60 is mounted upon. The motor 72 is fixedly mounted, but the drive roller 60 is pivotally mounted about the vertical axis 82 of the shaft 74 so that it pivots in a horizontal plane in a manner causing the drive roller 60 to move toward and away from the glass container 62. A spring 84 is used to bias the drive roller 60 to move about its pivot point in a manner urging the drive roller 60 toward the glass container 62. As mentioned above, the drive apparatus shown in FIGS. 2 and 3 is not as hard on the glass containers 62 in a high speed inspection line as the apparatus illustrated in FIG. 1, but it is mechanically complex, it has significant reliability issues, and it is expensive to manufacture.

Figure 4:
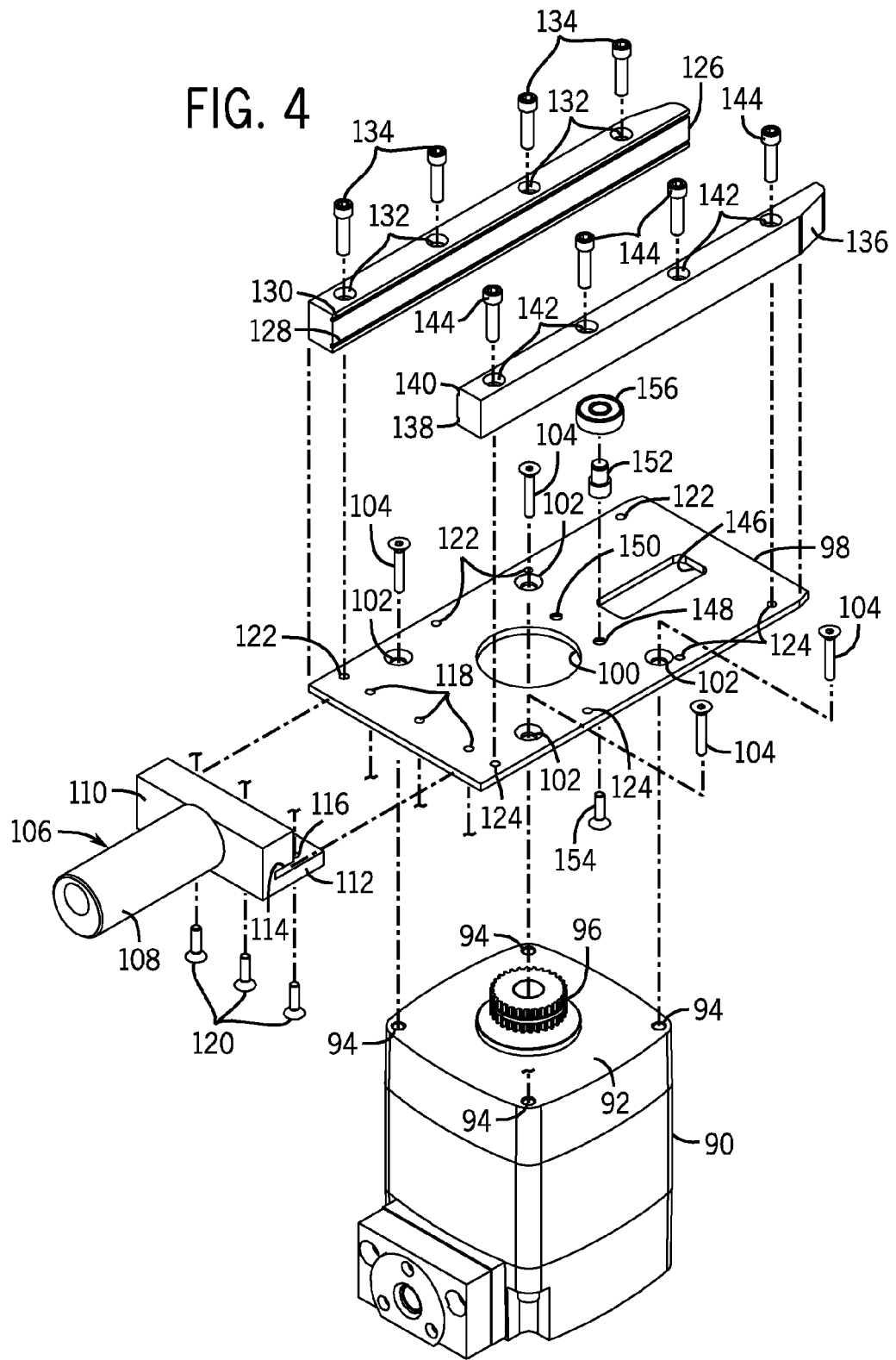
FIG. 4 is an exploded isometric view showing the various components of a body assembly of an apparatus for rotating glass containers that is constructed according to the teachings of the present invention.

Referring next to FIG. 4, the construction of a body assembly used by the apparatus for rotating glass containers and method of the present invention is illustrated. A motor assembly 90 has a flat, essentially rectangular housing top 92 with four threaded apertures 94 being respectively located at the four corners of the housing top 92. The motor assembly 90 has a drive belt pulley 96 mounted at the end of the motor shaft and extending above the housing top 92. The drive belt pulley 96 is a toothed pulley having an annular rib extending outwardly of the teeth at the centerline of the drive belt pulley 96. As will become evident below in conjunction with the discussion of FIG. 9, the drive belt pulley 96 is designed to accommodate a toothed belt having a longitudinally extending groove cut into the teeth of the toothed belt in the centerline thereof to accommodate the rib on the drive belt pulley 96.

Mounted onto the housing top 92 of the motor assembly 90 is a rectangular support plate 98 having a number of apertures located therein. The support plate 98 has a large circular aperture 100 located therein to accommodate the drive belt pulley 96 of the motor assembly 90 therethrough. There are four countersunk apertures 102 located around the machine head housing 100 in a pattern identical to the pattern of the four threaded apertures 94 located in the housing top 92 of the motor assembly 90. Four flathead bolts 104 are respectively inserted through the countersunk apertures 102 in the support plate 98 and then into the threaded apertures 94 in the housing top 92 of the motor assembly 90 to retain the support plate 98 on the motor assembly 90.

A mounting bracket 106 consisting of a cylindrical segment 108 extending from the midpoint of a rectangular block 110 having a flange 112 extending from the lower portion of the rectangular block 110 on the side opposite the cylindrical segment 108. A slot 114 is cut into the rectangular block 110 just above the flange 112, and three countersunk apertures 116 (only one is visible) are located in spaced-apart fashion in the flange 112. Additional details of the construction of the mounting bracket 106 will be described below in conjunction with the discussion of FIGS. 11 and 12. A proximal end of the support plate 98 has three threaded apertures 118 located therein in a pattern identical to the pattern of the three apertures 116 in the flange 112. The proximal end of the support plate 98 is inserted over the flange 112 into the slot 114 of the mounting bracket 106, and three flathead bolts 120 are respectively inserted through the countersunk apertures 116 in the flange 112 and then into the tapped apertures 118 in the support plate 98 to retain the support plate 98 on the mounting bracket 106.

Located in the support plate 98 near the left side thereof as viewed from the proximal end of the support plate 98 are four threaded apertures 122 that are located in spaced-apart fashion. Located in the support plate 98 near the right side thereof as viewed from the proximal end of the support plate 98 are four threaded apertures 124 that are located in spaced-apart fashion. There two sets of threaded apertures 122 and 124 will be used to mount guides on the sides of the support plate 98. The guides are handed, meaning that there can be two different configurations for their configuration depending upon the desired direction of rotation of the glass containers in the inspection station.

In the embodiment illustrated herein, it will be assumed that the glass containers will be rotated counterclockwise as viewed from above. Thus, the ware rotate wheel (not shown in FIG. 4) that imparts rotation to the glass container will rotate clockwise as viewed from above. Glass containers will enter the inspection station in which the apparatus for rotating glass containers is installed from the left as viewed from the apparatus for rotating glass containers toward the glass container in the inspection station, and glass containers will exit the inspection station to the right as viewed from the same perspective.

An upstream guide 126 will be installed on the left side of the support plate 98. The upstream guide 126 has a lower U-shaped guide slot 128 located on the side of the upstream guide 126 oriented toward the right side of the support plate 98 and near to the bottom side of the upstream guide 126. The upstream guide 126 also has an upper U-shaped guide slot 130 located on the same side of the upstream guide 126 and near to the top side of the upstream guide 126. The upstream guide 126 has four countersunk apertures 132 located therein in a pattern identical to the pattern of the four threaded apertures 122 located in the support plate 98 near the left side thereof. Four socket head cap screws 134 are respectively inserted through the countersunk apertures 132 in the upstream guide 126 and then into the threaded apertures 122 in the support plate 98 to retain the upstream guide 126 on the support plate 98.

A downstream guide 136 will be installed on the right side of the support plate 98. The downstream guide 136 has a lower U-shaped guide slot 138 located on the side of the downstream guide 136 oriented toward the upstream guide 126 on the left side of the support plate 98 and near to the bottom side of the downstream guide 136. The downstream guide 136 also has an upper L-shaped guide slot 140 located on the same side of the downstream guide 136 and open to the top side of the downstream guide 136. The downstream guide 136 has four countersunk apertures 142 located therein in a pattern identical to the pattern of the four threaded apertures 124 located in the support plate 98 near the right side thereof. Four socket head cap screws 144 are respectively inserted through the countersunk apertures 142 in the downstream guide 136 and then into the threaded apertures 124 in the support plate 98 to retain the downstream guide 136 on the support plate 98. Both the upstream guide 126 and the downstream guide 136 may be made of polymer material to reduce the impact forces experienced by the apparatus for rotating glass containers in operation.

It will at once be appreciated that the lower U-shaped guide slot 128 in the upstream guide 126 and the lower U-shaped guide slot 138 in the downstream guide 136 are respectively aligned to define a plane that is parallel to and spaced away from a plane defined by the upper surface of the support plate 98. Similarly, the upper U-shaped guide slot 130 on the downstream guide 136 and the upper L-shaped guide slot 140 in the downstream guide 136 are also respectively aligned to define a plane that is parallel to and spaced further away from the plane defined by the upper surface of the support plate 98. Also located in the support plate 98 between the circular aperture 100 and the distal end of the support plate 98 is an access aperture 146 the purpose for which will become evident below in conjunction with the discussion of FIG. 5.

Two countersunk apertures 148 and 150 are located in the support plate 98 between the circular aperture 100 and the access aperture 146. The countersunk apertures 148 and 150 are located on opposite sides of the centerline of the support plate 98, and only one will be used in a given implementation. For the example discussed herein where the glass containers will be rotated counterclockwise as viewed from above, the aperture 148, which is close to the right side of the support plate 98, will be used. A pulley support 152 is mounted on top of the support plate 98 using a flathead bolt 154 extending upwardly through the countersunk aperture 148 into the bottom of the pulley support 152. An idler pulley 156 is rotatably mounted on the pulley support 152.

Figure 5:
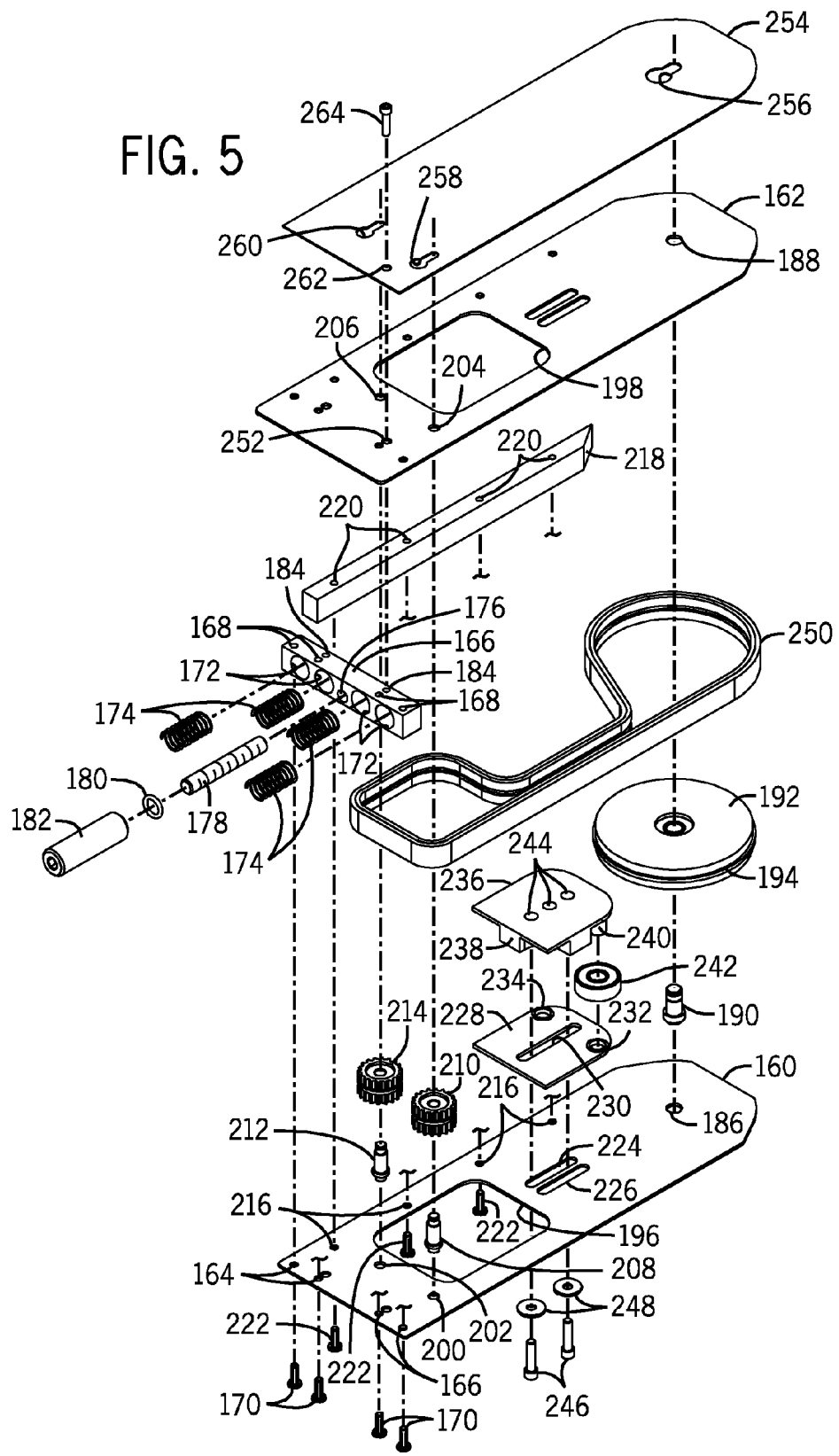
FIG. 5 is an exploded isometric view showing the various components of a carriage assembly of an apparatus for rotating glass containers that is constructed according to the teachings of the present invention and is for use with the body assembly shown in FIG. 4.

Referring next to FIG. 5, the construction of a carriage assembly used by the apparatus for rotating glass containers and method of the present invention which will be mounted on the body assembly illustrated in FIG. 4 is illustrated. The carriage assembly is built around a lower mainplate 160 and a spaced-apart upper mainplate 162. When the carriage assembly is installed into the body assembly, the side edges of the lower mainplate 160 will be received by the lower U-shaped guide slot 128 in the upstream guide 126 and the lower U-shaped guide slot 138 in the downstream guide 136, and the side edges of the upper mainplate 162 will be received by the upper U-shaped guide slot 130 in the upstream guide 126 and the upper L-shaped guide slot 140 in the downstream guide 136.

The lower mainplate 160 has four countersunk apertures 164 that are located in spaced-apart fashion near a proximal end of the lower mainplate 160. A rectangular rear spacer block 166 has four threaded apertures 168 located therein in a pattern identical to the pattern of the four countersunk apertures 164 located in the lower mainplate 160. Four flathead bolts 170 are respectively inserted through the countersunk apertures 164 in the lower mainplate 160 and then into the threaded apertures 168 in the rear spacer block 166 to retain the rear spacer block 166 on the lower mainplate 160.

The rear spacer block 166 has four cylindrical recesses 172 located in the distally facing side thereof, with four compression springs 174 each having an end placed into a corresponding one of the cylindrical recesses 172. A threaded aperture 176 is centrally located intermediate the cylindrical recesses 172, and has one end of a threaded rod 178 screwed therein. An elastomeric washer 180 is located on the threaded rod 178, and a cylindrical preload adjusting nut 182 having a threaded aperture in one end thereof and a hex head recess for receiving a hex head wrench in the opposite end thereof has its threaded end screwed onto the threaded rod 178. The use of the preload adjusting nut 182 to adjust the preload of the compression springs 174 will become evident below in conjunction with the discussion of FIGS. 11 and 12.

Two threaded apertures 184 are located in the top side of the rear spacer block 166 distal from the threaded apertures 168. The threaded apertures 184 are located on opposite sides of the centerline of the lower mainplate 160 and the rear spacer block 166. Only the one of the threaded apertures 184 closer to the right side of the lower mainplate 160 and the rear spacer block 166 as viewed from the proximal end to the lower mainplate 160 toward the distal end of the lower mainplate 160 will be used, with the one of the threaded apertures 184 that is used depending upon the direction in which the apparatus for rotating glass containers will rotate glass containers.

Corresponding apertures 186 and 188 are respectively centrally located in the lower mainplate 160 and the upper mainplate 162 near their respective distal ends. These apertures 186 and 188 are used to retain the respective ends of a support axle 190 about which a ware rotate wheel 192 will spin. The ware rotate wheel 192 is toothed with an annular rib 194 extending outwardly of the teeth at the centerline of the ware rotate wheel 192. The ware rotate wheel 192 may be made out of an elastomeric material such as, for example, polyurethane.

The lower mainplate 160 has a large rectangular aperture 196 located therein at a location closer to its proximal end than to its distal end. This rectangular aperture 196 is located to allow the drive belt pulley 96 and the idler pulley 156 of the body assembly illustrated in FIG. 4 to extend freely therethrough, and is sufficiently large to allow the lower mainplate 160 to be flipped around its centerline if the carriage assembly is to be converted to spin glass containers in the opposite direction. The upper mainplate 162 also has a large rectangular aperture 198 located therein at a location corresponding to the location of the rectangular aperture 196 in the lower mainplate 160.

Two apertures 200 and 202 are located in the lower mainplate 160 proximally of the rectangular aperture 196. The aperture 200 is located close adjacent the right edge of the lower mainplate 160, and the aperture 202 is located laterally just across the centerline of the lower mainplate 160 from the aperture 198. Two apertures 204 and 206 are located in the upper mainplate 162 in locations corresponding to the locations of the apertures 200 and 202 in the lower mainplate 160.

The apertures 200 and 204 are used to retain the respective ends of a support axle 208 about which an idler pulley 210 will spin. The apertures 202 and 206 are used to retain the respective ends of a support axle 212 about which an idler pulley 214 will spin. Both the idler pulley 210 and the idler pulley 214 are toothed pulleys having an annular rib extending outwardly of the teeth at the respective centerlines of the idler pulley 210 and the idler pulley 214. As such, the idler pulley 210 and the idler pulley 214 are designed to accommodate a toothed belt having a longitudinally extending groove cut into the teeth of the toothed belt in the centerline thereof to accommodate the ribs on the idler pulley 210 and the idler pulley 214.

Located in the lower mainplate 160 near the left side thereof are four countersunk apertures 216 that are located in spaced-apart fashion. A spacer block 218 will be installed on the left side of the lower mainplate 160. The spacer block 218 has four threaded apertures 220 located therein in a pattern identical to the pattern of the four countersunk apertures 216 located in the lower mainplate 160 near the left side thereof. Four flathead bolts 222 are respectively inserted through the countersunk apertures 216 in the lower mainplate 160 and then into the threaded apertures 220 in the spacer block 218 to retain the spacer block 218 on the lower mainplate 160. While four apertures are shown in the upper mainplate 162 in a pattern identical to the pattern of the four the countersunk apertures 216 in the lower mainplate 160, the flathead bolts 222 do not extend into the upper mainplate 162 since it is desirable to allow the upper mainplate 162 to be removable from the carriage assembly when the carriage assembly is installed on the body assembly.

Located in the lower mainplate 160 in a position distal of the rectangular aperture 196 are two slots 224 and 226, which are located on opposite sides of the centerline of the lower mainplate 160. Only one of the slots 224 and 226 will be used in a given implementation. For the example discussed herein where the glass containers will be rotated counterclockwise as viewed from above, the slot 224, which is closer to the left side of the lower mainplate 160, will be used. A belt tensioner assembly consisting of three parts will be used in conjunction with the slot 224.

The belt tensioner assembly has a tensioner plate 228 having a longitudinal slot 230 that is aligned in the same direction as the slot 224 in the lower mainplate 160. A circular recess 232 is located on the right of the slot 230 near the proximal end of the tensioner plate 228, and another circular recess 234a located on the left of the slot 230 near the proximal end of the tensioner plate 228. A tensioner carrier 236 has a centrally located wall 238 extending downwardly therefrom, which wall 238 will overlie the longitudinal slot 230 in the tensioner plate 228. A cylindrical support axle 240 extends downwardly from the bottom of the tensioner carrier 236 at the right side thereof and will extend into the circular recess 232 in the tensioner plate 228 when the tensioner carrier 236 is located on the tensioner plate 228. Another cylindrical support axle which is not visible extends downwardly from the bottom of the tensioner carrier 236 at the left side thereof and will extend into the circular recess 234 in the tensioner plate 228 when the tensioner carrier 236 is located on the tensioner plate 228.

An idler pulley 242 is rotatably mounted on the support axle 240 on the tensioner carrier 236, and is retained by the bottom of the support axle 240 fitting into the circular recess 232 when the tensioner carrier 236 is located on the tensioner plate 228. There are threaded apertures 244 extending through the tensioner carrier 236 within the wall 238. A pair of bolts 246 having washers 248 respectively located thereupon extend through the slot 224 in the lower mainplate 160, through the longitudinal slot 230 in the tensioner plate 228, and into two of the threaded apertures 244. It will be appreciated that the longitudinal position of the belt tensioner assembly, and thus of the idler pulley 242, on the lower mainplate 160 is adjustable.

A ware rotate belt 250 is shown in the configuration that it will be mounted in for the configuration shown (with the glass containers being rotated counterclockwise as viewed from above). Its installation onto the various components will be described below in conjunction with the discussion of FIG. 7. The upper mainplate 162 will be mounted above the lower mainplate 160, with the proximal end of the upper mainplate 162 overlying the rear spacer block 166. In this position, an aperture 252 in the upper mainplate 162 will overlie the threaded aperture 184 in the rear spacer block 166. The top portions of the support axle 190, the support axle 208, and the support axle 212 will extend through the apertures 188, the aperture 204, and the aperture 206 in the upper mainplate 162.

Located at the top ends of each of the support axle 190, the support axle 208, and the support axle 212 is a keyhole standoff that has an annular recess machined therein. The open portions of the upper mainplate 162 will be enclosed by a cover 254, with keyhole apertures 256, 258, and 260 being located in the cover 254 in locations corresponding with the apertures 188, 204, and 206 in the upper mainplate 162. The keyhole standoffs at the top ends of the support axle 190, the support axle 208, and the support axle 212 thus engage the keyhole apertures 256, 258, and 260 to lock the cover 254 in place on top of the upper mainplate 162. An aperture 262 in the cover 254 overlies the aperture 252 in the upper mainplate 162 when the cover 254 is locked in place on the upper mainplate 162. A bolt 264 extends through the aperture 262 in the cover 254, the aperture 252 in the upper mainplate 162, and into the threaded aperture 184 in the rear spacer block 166.

Figure 6:
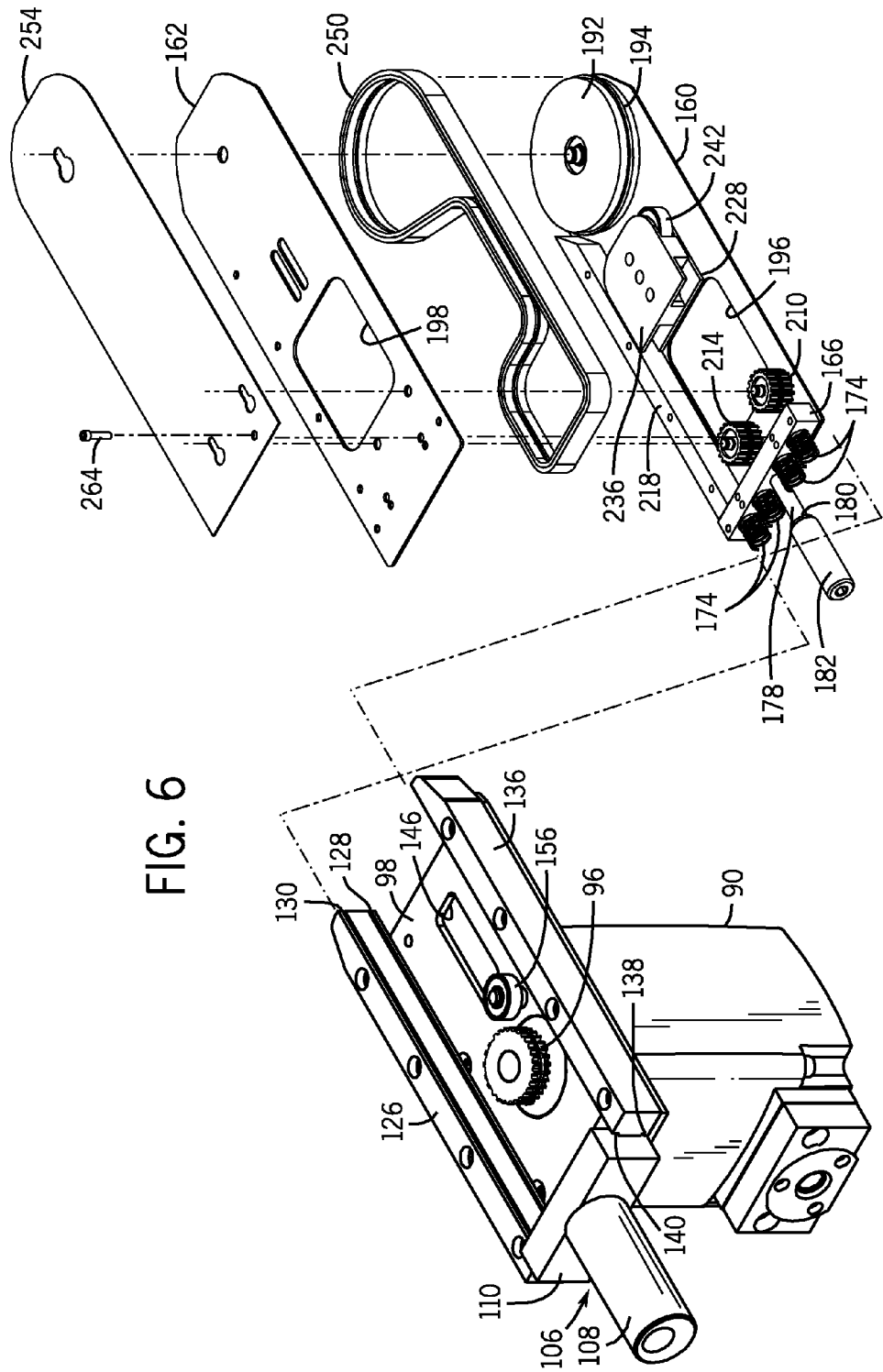
FIG. 6 is a partially exploded isometric view showing the assembly of the carriage assembly illustrated in FIG. 5 onto the body assembly illustrated in FIG. 4, with the carriage assembly not yet installed onto the body assembly.

Referring now to FIG. 6, the assembled body assembly is shown at the left and the mostly assembled carriage assembly is shown at the right. However, in order to facilitate the installation of the carriage assembly onto the body assembly, the upstream guide 126, the downstream guide 136, and the mounting bracket 106 are best removed from the support plate 98 of the body assembly. The lower mainplate 160 will also have the elastomeric washer 180 and the preload adjusting nut 182 removed from the threaded rod 178.

The lower mainplate 160 of the carriage assembly may be lowered onto the support plate 98 of the body assembly, with the drive belt pulley 96 and the idler pulley 156 of the body assembly extending through the rectangular aperture 196 in the lower mainplate 160. The upstream guide 126 and the downstream guide 136 may then be placed into position on the support plate 98 with the left side of the lower mainplate 160 being located in the lower U-shaped guide slot 128 in the upstream guide 126, and with the right side of the lower mainplate 160 being located in the upper L-shaped guide slot 140 in the downstream guide 136.

The mounting bracket 106 may be returned to its position on the support plate 98, with the threaded rod 178 extending into the cylindrical segment 108 of the mounting bracket 106 (the configuration of the interior of the cylindrical segment 108 will be discussed below in conjunction with the discussion of FIGS. 11 and 12). Each of the upstream guide 126, the downstream guide 136, and the mounting bracket 106 are then attached to the support plate 98 by the installation of their respective hardware to retain them in there respective positions. The elastomeric washer 180 and the preload adjusting nut 182 may then be returned to their respective positions on the threaded rod 178, which is located within the cylindrical segment 108.

Figure 7:
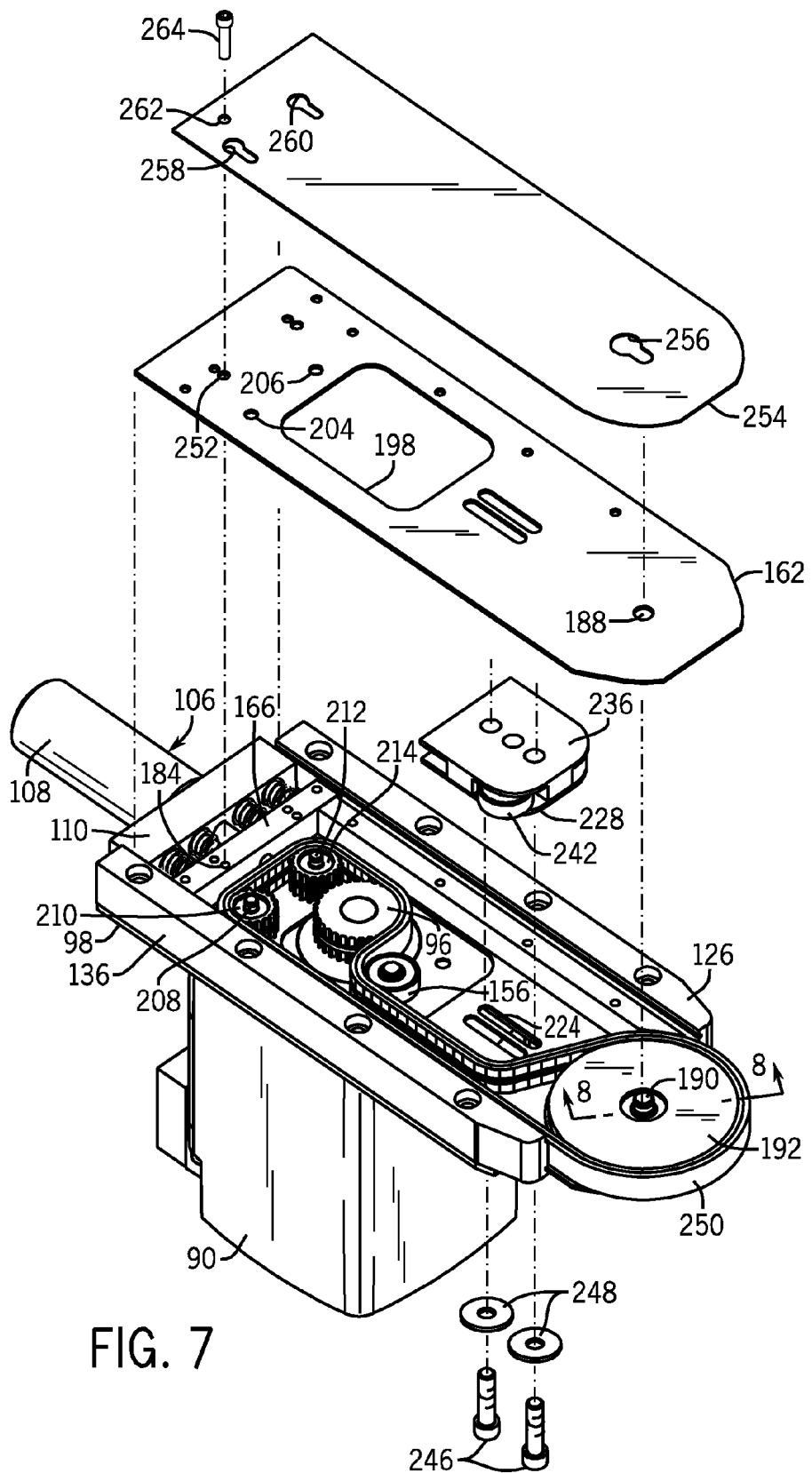
FIG. 7 is a partially exploded isometric view showing the carriage assembly and the body assembly illustrated in FIG. 6, with the carriage assembly partially installed in the body assembly.

Referring next to FIG. 7, the installation of the ware rotate belt 250 is illustrated. It may facilitate the installation of the ware rotate belt 250 to remove the belt tensioner assembly (which includes the tensioner plate 228, the tensioner carrier 236, and the idler pulley 242) from the carriage assembly by removing the two bolts 246 and their washers 248. As mentioned above, the ware rotate wheel 192, the idler pulley 210, and the idler pulley 214, which will be located on the inside of the ware rotate belt 250, are toothed with an annular rib extending outwardly of the teeth at the centerline. The idler pulley 156 and the idler pulley 242, which will be located on the outside of the ware rotate belt 250, are not toothed.

Figure 8:
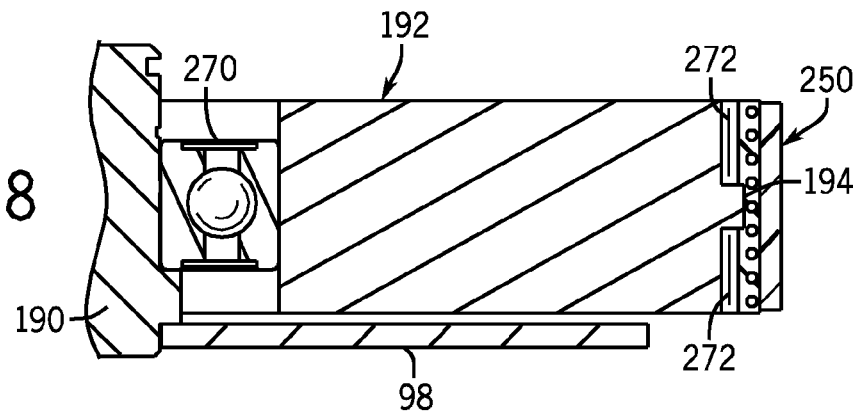
FIG. 8 is a cross-sectional partial view showing a portion of the ware rotate belt and a portion of the ware rotate wheel.
Figure 9:
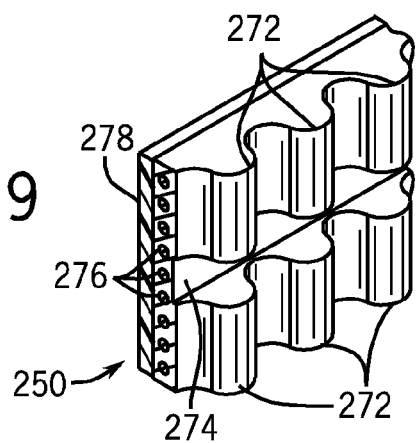
FIG. 9 is an isometric cross-sectional view of the ware rotate belt.

Referring briefly to FIG. 8, a partial cross section of the ware rotate wheel 192 with the ware rotate belt 250 thereupon is illustrated. The ware rotate wheel 192 is mounted on the support axle 190 with a bearing 270. Referring to FIG. 9 in addition to FIG. 8, a more detailed view of a portion of the ware rotate belt 250 is illustrated. The ware rotate belt 250 has teeth 272 into which a longitudinally extending groove 274 has been cut at the centerline of the ware rotate belt 250.

The teeth 272 may be made of neoprene, and the ware rotate belt 250 has reinforcing fibers 276 located therein that may be made of fiberglass or a para-aramid synthetic fiber such as the material marketed by DuPont under the trademark KEVLAR. The ware rotate belt 250 has a cover material 278 on the side opposite the teeth 272 that is the surface which will contact and rotate glass containers. This cover material 278 may be made of a resilient, high coefficient of friction material such as neoprene, white rubber, non-marking rubber, or like materials to provide a good surface to contact glass containers. The ware rotate belt 250 should be of seamless construction to maximize its operating life.

Referring again to FIG. 7, the ware rotate belt 250 is installed with the teeth 272 engaging the ware rotate wheel 192, the drive belt pulley 96, the idler pulley 210, and the idler pulley 214, and with the back side of the ware rotate belt 250 bearing against the idler pulley 156 and the idler pulley 242. The longitudinal position of the belt tensioner assembly (which includes the tensioner plate 228, the tensioner carrier 236, and the idler pulley 242) may be adjusted to place the proper tension on the ware rotate belt 250, and the bolts 246 are tightened to lock the belt tensioner assembly in place.

Figure 10:
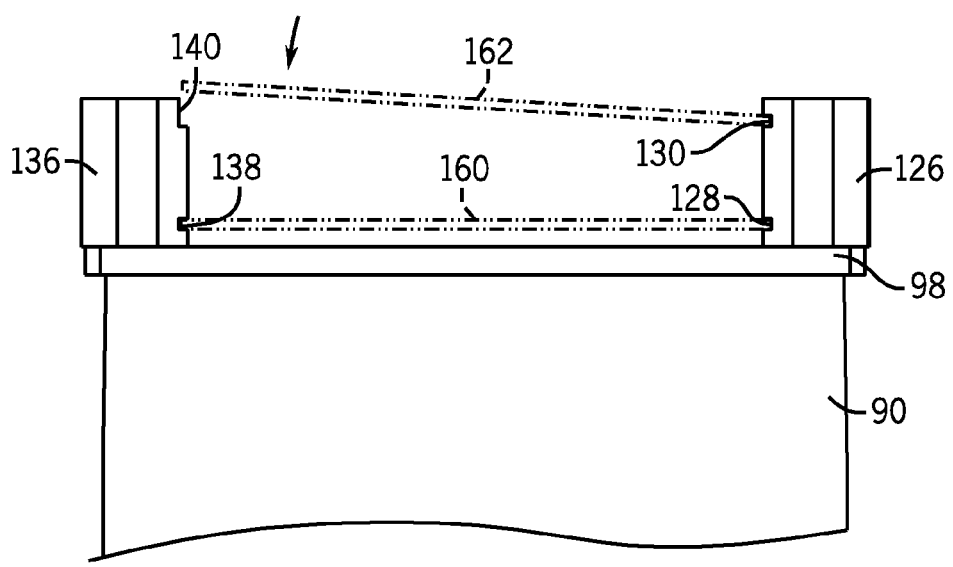
FIG. 10 is an end view of the body assembly showing the installation of the upper mainplate of the carriage assembly thereupon.

Referring now to FIG. 10 in conjunction with FIG. 7, the installation of the upper mainplate 162 and the cover 254 onto the carriage assembly and the body assembly is illustrated. The left side of the upper mainplate 162 (shown from the distal end on the right side in FIG. 10) is inserted into the upper U-shaped guide slot 130 in the upstream guide 126 of the body assembly. The right side of the upper mainplate 162 (shown from the distal end on the left side in FIG. 10) is then lowered into the upper L-shaped guide slot 140 in the downstream guide 136 of the body assembly. As it is lowered, the upper ends of the support axle 190, the support axle 208, and the support axle 212 will be respectively received and extend through the aperture 188, the aperture 204, and the aperture 206 in the upper mainplate 162.

The cover 254 is then lowered onto the carriage assembly, with the top ends of each of the support axle 190, the support axle 208, and the support axle 212 being respectively received by the keyhole apertures 256, 258, and 260 in the larger diameter portions thereof. The cover 254 may then be moved in a distal direction, with the annular recesses at the top ends of the support axle 190, the support axle 208, and the support axle 212 being respectively received by the smaller diameter portions of the keyhole apertures 256, 258, and 260, thereby retaining the cover 254 on the carriage assembly. The cover 254 is then locked into position by inserting 264 through the aperture 262 in the cover 254, the aperture 252 in the upper mainplate 162, and then screwing it into the threaded aperture 184 in the rectangular block 110.

Figure 11:
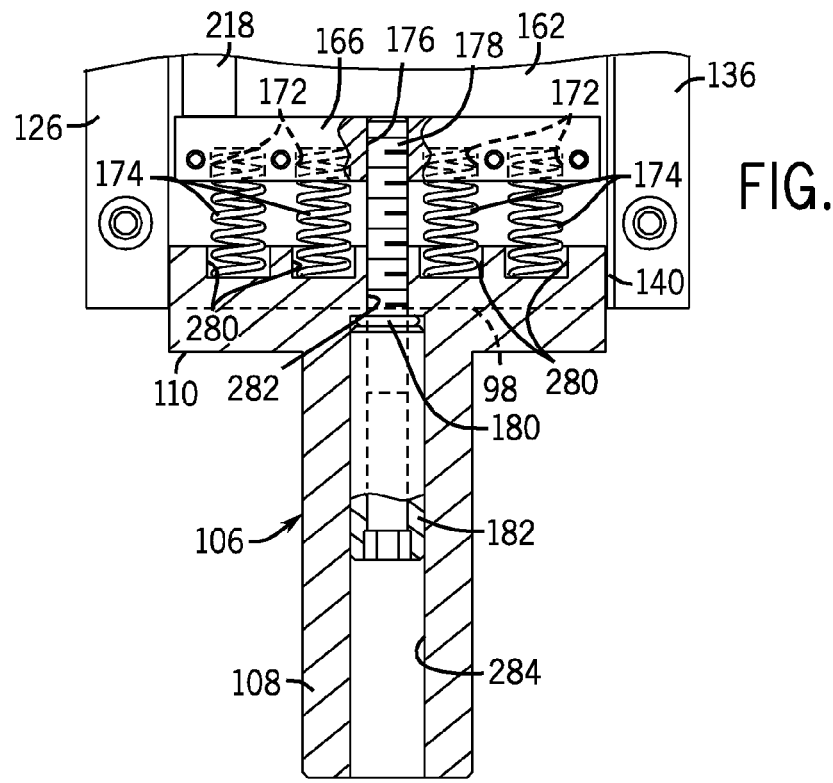
FIG. 11 is a cutaway view of portions of the carriage assembly and the body assembly showing the springs used to preload the carriage assembly.
Figure 12:
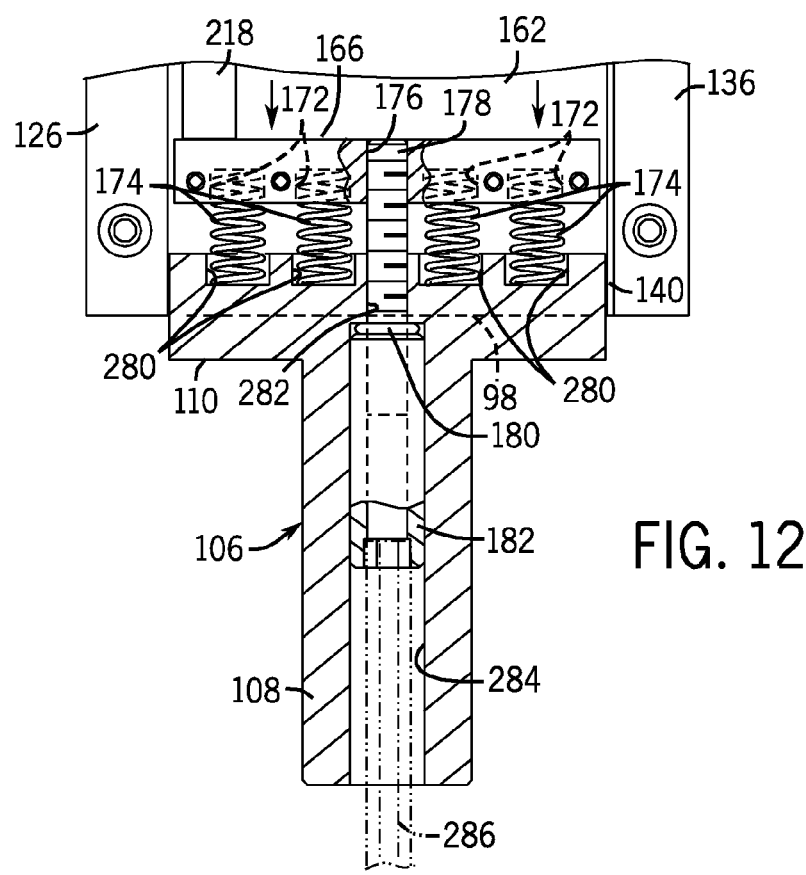
FIG. 12 is a cutaway view of portions of the carriage assembly and the body assembly similar to that shown in FIG. 11, showing the preload tension of the springs being adjusted.

Referring next to FIGS. 11 and 12, the construction and adjustment of the biasing of the carriage assembly with respect to the base assembly is illustrated. As mentioned above with reference to FIG. 5, the four compression springs 174 each have an end located in one of the four cylindrical recesses 172 located in the proximally facing side of the rear spacer block 166. The rectangular block 110 also has four cylindrical recesses 280 that are located in the proximally facing side thereof that are aligned with the four cylindrical recesses 172 in the rear spacer block 166, with the four compression springs 174 each having their other end placed into a corresponding one of the cylindrical recesses 280.

A passageway is located through the cylindrical segment 108 of the mounting bracket 106 and extends through the rectangular block 110 of the mounting bracket 106. This passageway consists of two segments, with a first smaller diameter cylindrical passageway 282 extending nearly through the rectangular block 110, and a second larger diameter cylindrical passageway 284 extending the rest of the way through the rectangular block 110 and throughout the entire length of the cylindrical segment 108. The threaded rod 178, which has an end screwed into the threaded aperture 176 in the rear spacer block 166, extends through the cylindrical passageway 282 and well into the cylindrical passageway 284.

The elastomeric washer 180 and the preload adjusting nut 182 are inserted through the cylindrical passageway 284 and are placed onto the threaded rod 178. Thus, by using a hex head tool 286, the preload adjusting nut 182 may be turned to adjust the precompression on the compression springs 174. The force that may be exerted upon a glass container by the apparatus for rotating glass containers of the present invention may thereby be varied.

When no glass bottle is present at an inspection station, the compression springs 174 will urge the carriage assembly forward until the elastomeric washer 180 reaches the end of the cylindrical passageway 284 and halts the travel of the carriage assembly. The preload adjusting nut 182 is thus positioned to limit the travel of the carriage assembly. As the amount of carriage assembly travel is decreased, the compression springs 174 are preloaded more heavily. By using the preload adjusting nut 182 and the position of the rotate head in its mounting post the one may control the initial contact force of the ware rotate wheel 192, which has the ware rotate belt 250 thereabout, and the glass container 290 as well as the amount of travel the carriage assembly will experience as the glass container 290 enters, rotates in, and exits the inspection station. The contact force and carriage assembly travel should be adjusted to apply the minimum force and use the minimum travel that will reliably rotate the glass container 290.

Figure 13:
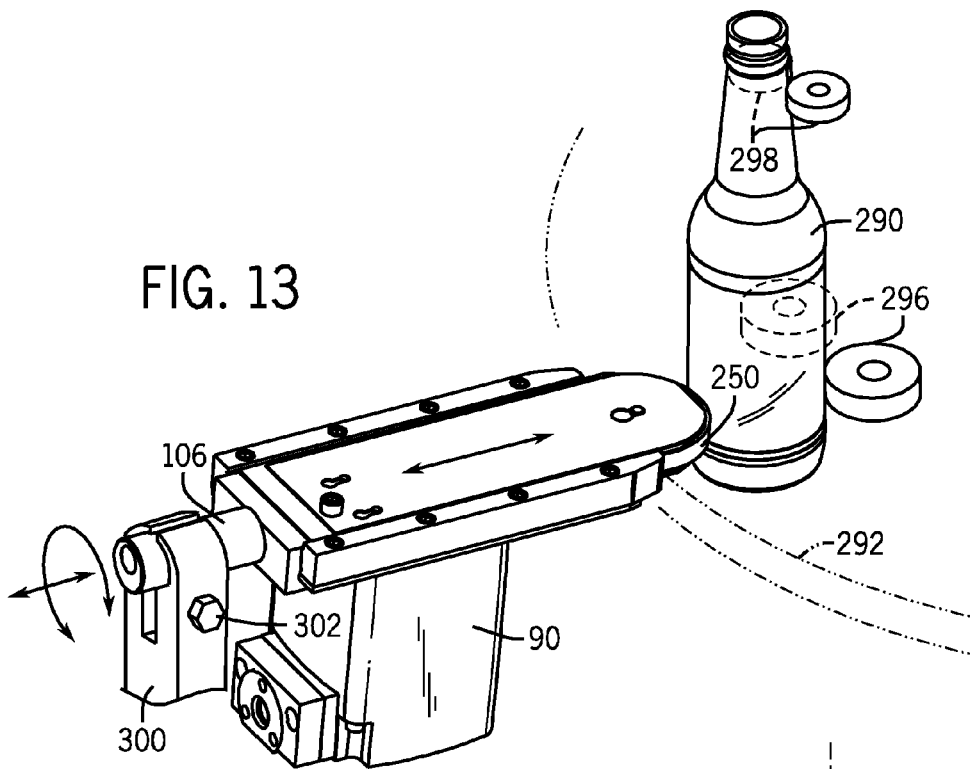
FIG. 13 is an isometric view showing the installation of the apparatus for rotating glass containers of the present invention being adjustably mounted on a support member in position to rotate a glass container.
Figure 14:
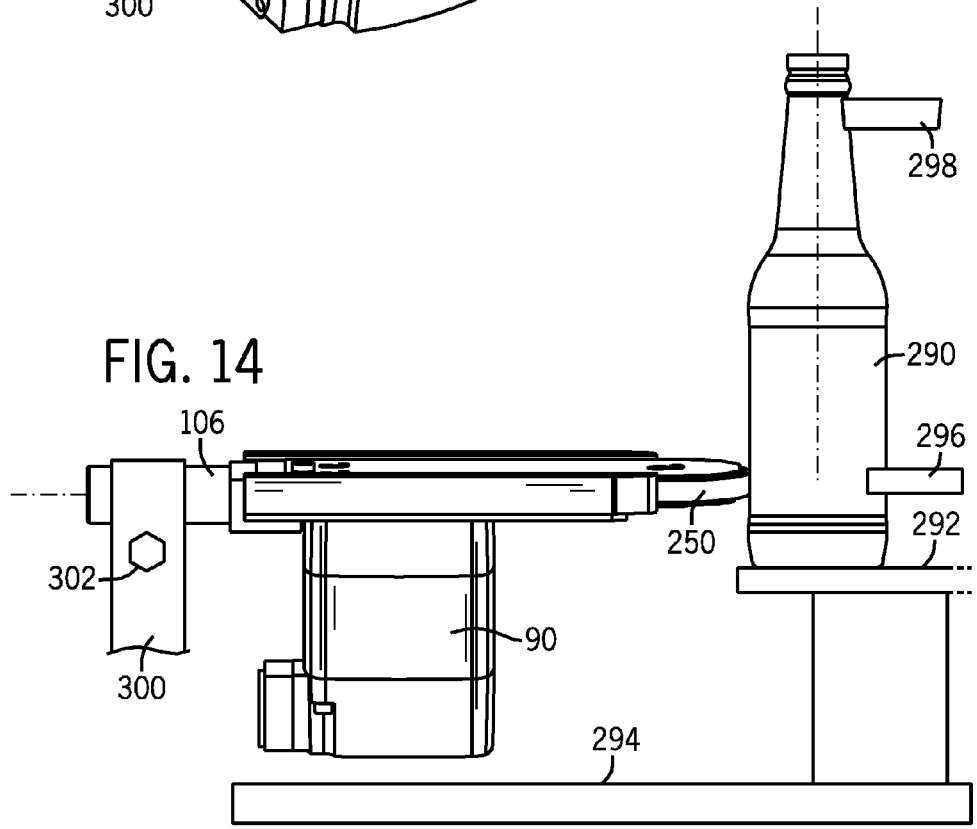
FIG. 14 is a side view showing the slight tilting of the apparatus for rotating glass containers of the present invention to cause a downwardly acting force to be imparted to the glass container.

Referring now to FIGS. 13 and 14, the installation of the apparatus for rotating glass containers of the present invention into a production line is illustrated. A glass container 290 is supported on a deadplate 292 that is located above a top plate 294, with the glass container 290 being supported for rotation on one side thereof near its bottom by a pair of rollers 296 and near its top by a second pair of rollers 298. The distal end of the apparatus for rotating glass containers of the present invention is brought into contact with the glass container 290 on the side thereof opposite the rollers 296 and the rollers 298. It will be appreciated that the distal portion of the ware rotate wheel 192, which has the ware rotate belt 250 thereabout, will contact the glass container 290 to rotate it.

The apparatus for rotating glass containers of the present invention is supported by a support member 300 that is fixedly mounted an one end (not shown herein). The other end of the support member 300 has a split construction and receives the cylindrical segment 108 of the mounting bracket 106 of the base assembly therein. It will be appreciated that the apparatus for rotating glass containers of the present invention may be both rotated about the axis of the cylindrical segment 108 and longitudinally adjusted to move distal portion of the ware rotate wheel 192, which has the ware rotate belt 250 thereabout, closer to or further away from the glass container 290. The support member 300 has a locking bolt 302 that may be used to lock the cylindrical segment 108 and the apparatus for rotating glass containers of the present invention into a desired position.

It will be appreciated by those skilled in the art that neither the rollers 296 and the rollers 298 nor the ware rotate wheel 192, with the ware rotate belt 250 thereabout, act to retain the glass container 290 on the deadplate 292 as it is rotated. In order to ensure that the base of the glass container 290 will remain in contact with the deadplate 292, it is desirable to angle the apparatus for rotating glass containers of the present invention to ensure that the movement of the ware rotate belt 250 imparts a downward force to the glass container 290 as it rotates the glass container 290. An angle of no more than two degrees from horizontal has been found to be adequate, with the downward angle being in the direction of movement of the ware rotate belt 250 with respect to the surface of the glass container 290.

Figure 15:
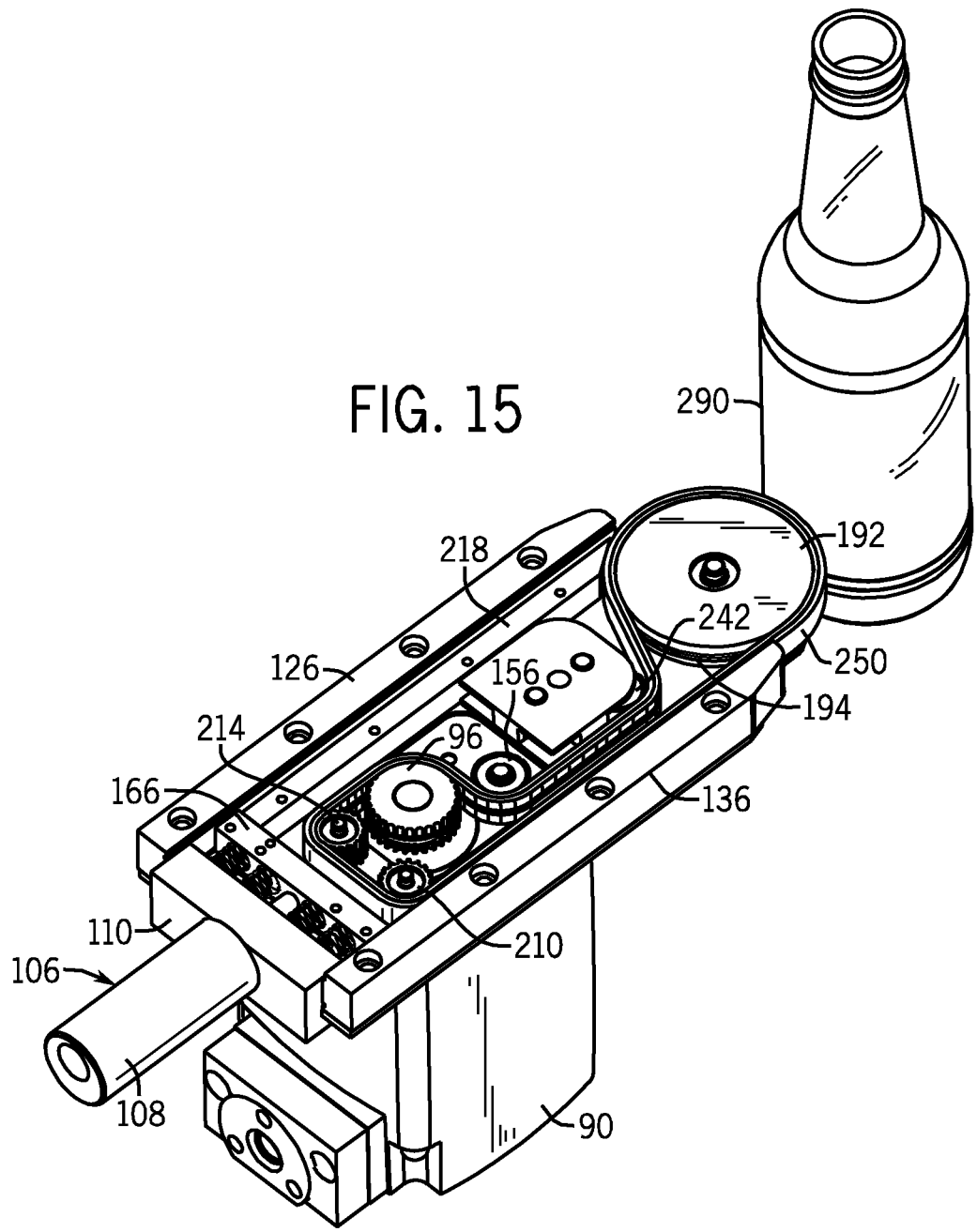
FIG. 15 is an isometric view of the apparatus for rotating glass containers of the present invention in position to rotate a glass container, with the cover plate and the upper main plate removed for clarity.
Figure 16:
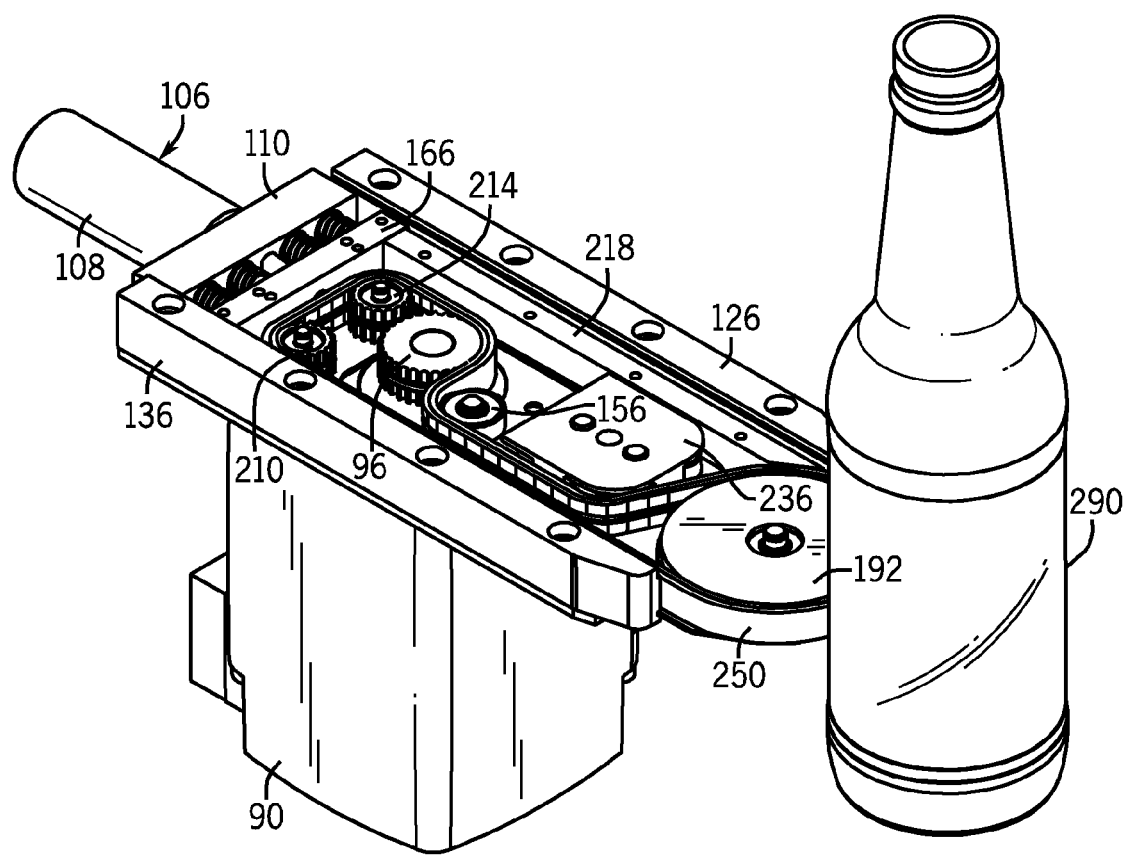
FIG. 16 is an isometric view similar to that of FIG. 15, but from a different angle.

Referring next to FIGS. 15 through 18, the apparatus for rotating glass containers of the present invention is shown in position to rotate the glass container 290. FIGS. 15 and 16 are shown with the upper mainplate 162 and the cover 254 removed to show the path of the ware rotate belt 250 around the ware rotate wheel 192 to rotate the glass container 290, and particularly show the use of the belt tensioner assembly (which includes the tensioner plate 228, the tensioner carrier 236, and the idler pulley 242) to maintain proper tension in the ware rotate belt 250. They also demonstrate how the presence of the annular rib 194 on the ware rotate wheel 192 and the annular ribs respectively located at the centerlines of the teeth on each of the drive belt pulley 96 and the idler pulleys 210 and 212 interact with the groove 274 located at the centerline of the ware rotate belt 250 intermediate the teeth 272 to retain the ware rotate belt 250 in place on its support system.

FIGS. 17 and 18 demonstrate the extremely limited amount of space that the apparatus for rotating glass containers of the present invention takes up, with the entire apparatus having a width that is little more than the diameter of the ware rotate wheel 192 and the thickness of the ware rotate belt 250, particularly at the point the apparatus contacts the glass container 290 to rotate it. Since the apparatus for rotating glass containers of the present invention is also very thin, due in large part to the design of the apparatus using the ware rotate wheel 192 and the ware rotate belt 250, it has a very small footprint. FIG. 18 also shows the access to the bolts 246 through the access aperture 146 in the support plate 98 to adjust the belt tensioner assembly (which includes the tensioner plate 228, the tensioner carrier 236, and the idler pulley 242).

Figure 19:
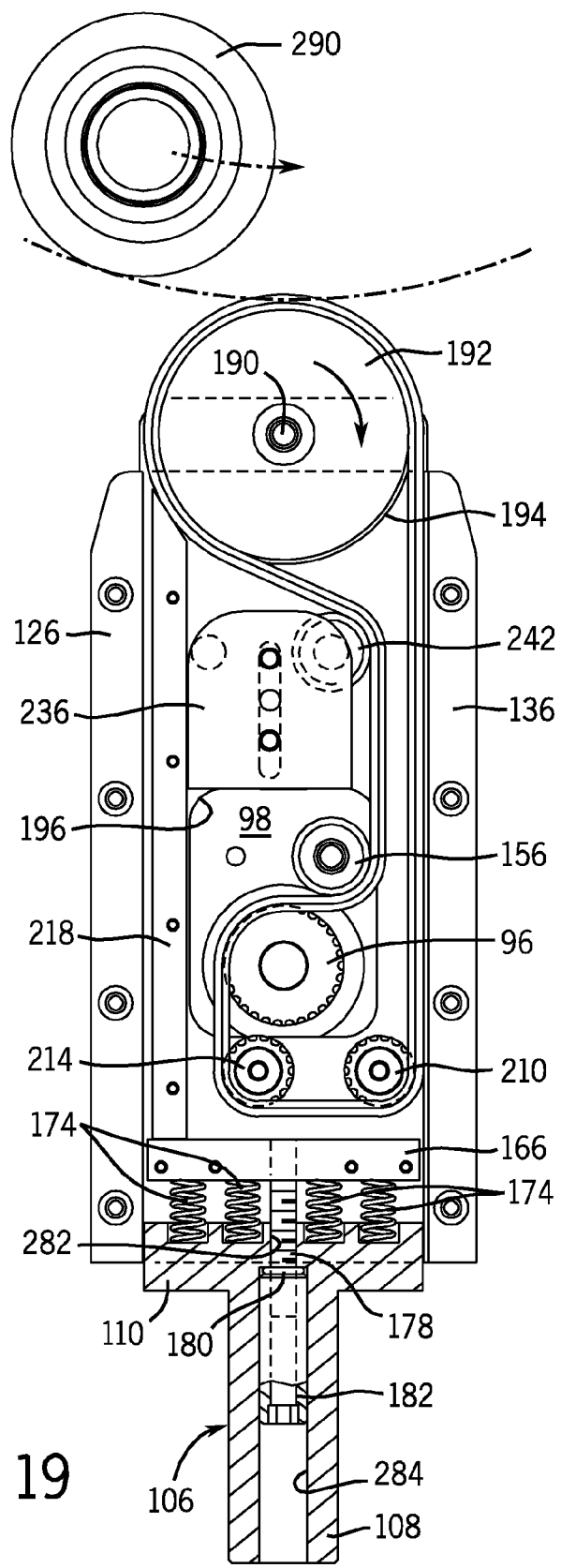
FIG. 19 is a top plan view of the fully assembled apparatus for rotating glass containers of the present invention, with the cover plate and the upper main plate removed for clarity, showing the position of the ware rotate belt and the ware rotate wheel with respect to the position of a glass container being brought into the inspection station.
Figure 20:
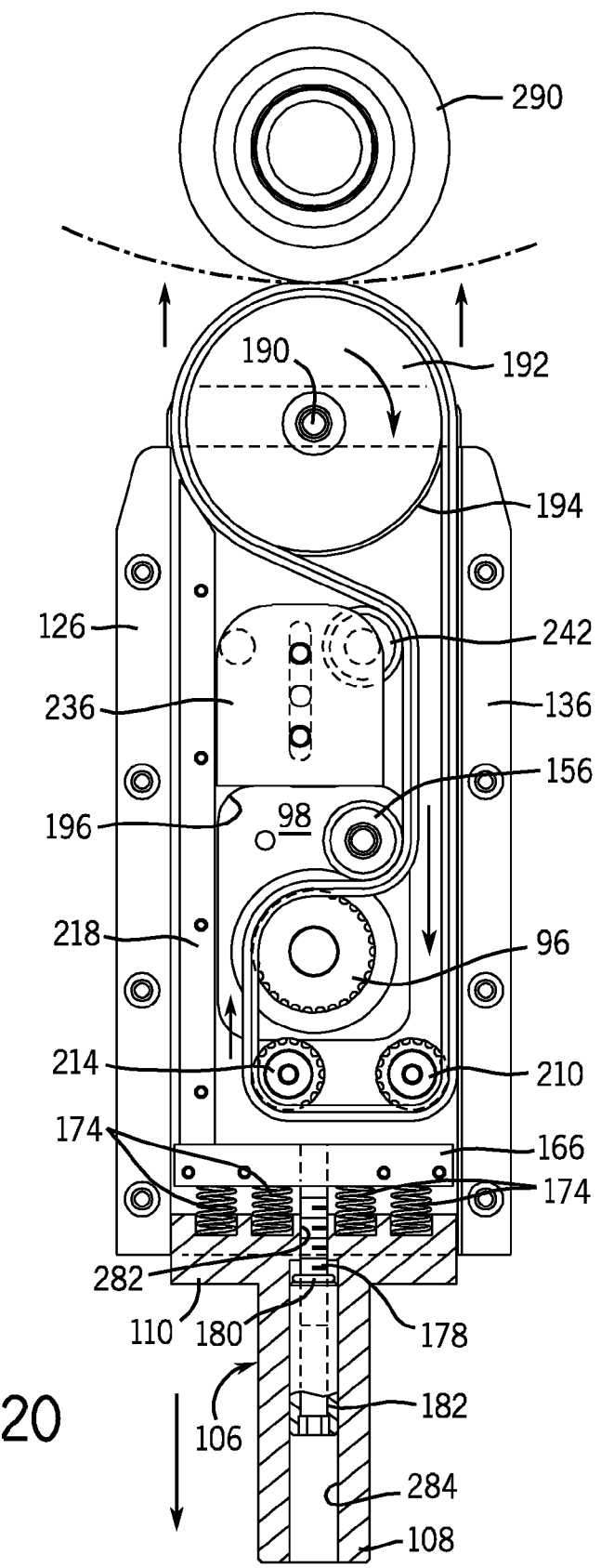
FIG. 20 is a top plan view similar to that of FIG. 19, showing the tension caused in the ware rotate belt by the initial inertia of the glass container as it resists rotation, as well as the movement by the carriage assembly toward the ware rotate belt caused by the increased tension in the ware rotate belt.
Figure 21:
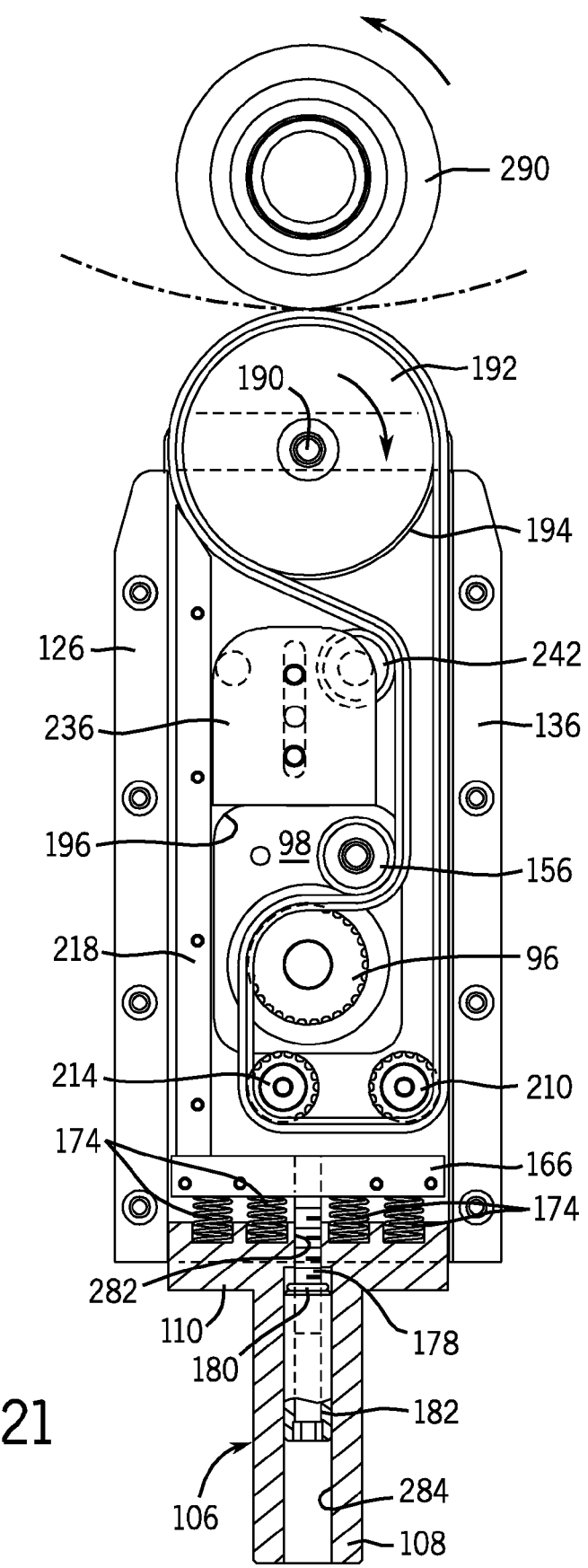
FIG. 21 is a top plan view similar to that of FIGS. 19 and 20, showing the glass container being rotated at full speed by the ware rotate belt and the ware rotate wheel, with increased tension in the ware rotate belt no longer existing in the ware rotate belt and the carriage assembly having moved back to lower the pressure exerted on the glass container.

Referring finally to FIGS. 19 through 21, the apparatus for rotating glass containers of the present invention is shown in operation rotating the glass container 290. FIG. 19 shown the glass container 290 in the process of being rotated into an inspection station position, FIG. 20 shows the glass container 290 have been brought into the inspection station position but not having been accelerated up to full rotation speed, and FIG. 21 shows the glass container 290 in the inspection station at full rotation speed.

It may be seen in FIG. 19 that the carriage assembly has been urged forward by the compression springs 174 to the position wherein the elastomeric washer 180 has reached the end of the cylindrical passageway 284 and halted the travel of the carriage assembly. In this position, it may be noted that the ware rotate belt 250 and the ware rotate wheel 192 are located inside the position that the glass container 290 will be when it is in the inspection station.

In FIG. 20, the glass container 290 is in position in the inspection station, but has not yet been spun up to full rotation speed, due primarily to the inertia of the glass container 290. It may be seen that the carriage assembly has retracted somewhat due to the force exerted by the glass container 290 against the ware rotate belt 250 and the ware rotate wheel 192. The compression springs 174 urge the carriage assembly including the center portion of the ware rotate wheel 192 and the portion of the ware rotate belt 250 around it into contact with the glass container 290.

As the moving ware rotate belt 250 begin to cause the glass container 290 to rotate (but the glass container 290 is not rotating at full speed), the portion of the ware rotate belt 250 extending from the ware rotate wheel 192 around the idler pulley 210 and 214 and to the drive belt pulley 96 becomes more highly loaded, increasing the tension in this segment of the ware rotate belt 250. The increased tension in the ware rotate belt 250 now pulls the only part of this drive belt path than can move, the portion between the idler pulley 214 (mounted on the lower mainplate 160 of the carriage assembly) and the drive belt pulley 96 (mounted on the motor assembly 90 of the base assembly) pulls the carriage assembly in a distal direction, causing the ware rotate belt 250 and the ware rotate wheel 192 to be driven into the glass container 290 with more force.

As the glass container 290 approaches its final rotating speed, the tension in the ware rotate belt 250 drops, leaving the compression springs 174 as the only force that is acting to drive the carriage assembly into the ware. This self-energizing effect of this ware rotate belt 250 geometry makes it possible for the apparatus for rotating glass containers to operate at a lower, time weighted average contact force exerted against the glass container 290 (which, of course, will increase the life of the components of the apparatus for rotating glass containers of the present invention).

It may therefore be appreciated from the above detailed description of the exemplary embodiments of the present invention that it teaches an apparatus for rotating glass containers of the present invention is highly compact, enabling it to consume minimal volume in the area near the glass container being rotated to thereby allow the maximum amount of room possible for inspection apparatus. Despite the compact size of the apparatus for rotating glass containers of the present invention, it has the ability to supply sufficient torque to the glass container to accelerate it rapidly to minimize the time required to inspect each glass container. The apparatus for rotating glass containers of the present invention presents a highly compliant drive surface and also provides an increased capacity to quickly "nip" the outer wall of the glass container to rapidly overcome its inertia and spin it up to speed.

The apparatus for rotating glass containers of the present invention presents a low degree of impact to glass containers, and has an outstanding ability to move quickly into contact with the glass container without damaging it or being damaged by it. The apparatus for rotating glass containers of the present invention is also capable of imparting a downwardly acting force to the glass container, thereby acting to restrain it downwardly as it is being rotated at high speed. The apparatus for rotating glass containers of the present invention is of robust mechanical design and of high reliability to avoid any loss of production occasioned by it failing.

The apparatus for rotating glass containers of the present invention is of a construction which is both durable and long lasting and has construction characteristics that allow it to be serviced quickly, and it will require only relatively infrequent maintenance to be provided by the user throughout its operating lifetime. The apparatus for rotating glass containers of the present invention is also of inexpensive construction to enhance its market appeal and to thereby afford it the broadest possible market. Finally, all of the aforesaid advantages and objectives of the apparatus for rotating glass containers and method of the present invention are achieved without incurring any substantial relative disadvantage.

Although the foregoing description of the apparatus for rotating glass containers and method of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. An apparatus for rotating glass containers that are sequentially indexed into and out of an inspection station supporting a glass container to be inspected in vertical fashion on a surface, the inspection station having rollers for supporting the glass container in the inspection station for rotation on a side opposite a side of the glass container to be engaged by said apparatus for rotating glass containers, said apparatus for rotating glass containers comprising:

a base member for installation in an adjustably fixed position with respect to the inspection station on the side of the glass container in the inspection station opposite the side of the glass container supported by the rollers;

a pair of guides coupled to the base member;

a carriage member slidingly mounted between the pair of guides coupled to said base member in a linearly moveable fashion, relative to the base member, toward and away from the glass container in the inspection station, said carriage member having opposite proximal and distal ends, said distal end being closest to the inspection station and said proximal end being furthest from the inspection station;

a ware rotate wheel that is rotatably mounted on said carriage member near said distal end thereof such that a portion of said ware rotate wheel extends outwardly proximate said distal end of said carriage member;

a motor having a drive belt pulley driven by said motor; and a ware rotate belt mounted on said drive belt pulley and said ware rotate wheel, said motor thereby driving both said ware rotate belt and said ware rotate wheel with the ware rotate belt configured to pull the whole carriage member toward the glass container as belt tension increases;

wherein a portion of said ware rotate belt is located upon the portion of said ware rotate wheel that extends outwardly proximate said distal end of said carriage member, said ware rotate belt contacting the side of the glass container in the inspection station opposite the side of the glass container supported by the rollers to rotate the glass container.

2. An apparatus as defined in claim 1, wherein said base member comprises:

a mounting bracket secured to a support member in a manner allowing linear movement by said carriage member toward and away the inspection station as well as rotational movement of said carriage member about an axis parallel to an axis of said linear movement by said carriage member toward and away the inspection station.

3. An apparatus as defined in claim 2, wherein rotational movement of the carriage member is adjusted such that said ware rotate wheel and said portion of said ware rotate belt located upon the portion said ware rotate wheel that extends outwardly proximate said distal end of said carriage member are in a plane angled approximately two degrees or less from a horizontal plane to cause the movement of said ware rotate belt to impart a downward force to the glass container in the inspection station as the container is rotated.

4. An apparatus as defined in claim 1, wherein said guides are located at respective sides of said carriage member and wherein said guides are made of a polymer material to reduce the impact forces experienced by said apparatus in operation.

5. An apparatus as defined in claim 1, additionally comprising:

biasing apparatus that applies a force to said carriage to urge the carriage distal end toward the glass container in the inspection station.

6. An apparatus as defined in claim 5, wherein said biasing apparatus comprises:

a mounting bracket mounted on said base member near an end thereof that is furthest from the inspection station;

a rear spacer block mounted at said proximal end of said carriage member; and at least one spring located between said mounting bracket and said rear spacer block.

7. An apparatus as defined in claim 6, wherein the position of said mounting bracket on said base member is linearly moveable toward and away the inspection station to vary the force applied to said carriage to urge the distal end of the carriage toward the glass container in the inspection station.

8. An apparatus as defined in claim 1, wherein said ware rotate wheel is made out of an elastomeric material such as polyurethane.

9. An apparatus as defined in claim 1, wherein said ware rotate wheel and said drive belt pulley are toothed to engage teeth that are located on an inside surface of said ware rotate belt.

10. An apparatus as defined in claim 9, wherein said ware rotate wheel and said drive belt pulley each have an annular rib that extends outwardly of said teeth at a centerline of each; and a longitudinally extending groove cut into said teeth on said inside surface of said ware rotate belt at the centerline of said ware rotate belt.

11. An apparatus as defined in claim 9, wherein said teeth of said ware rotate belt are made of neoprene, and wherein said ware rotate belt has reinforcing fibers located therein.

12. An apparatus as defined in claim 1, wherein said ware rotate belt has an outside surface made of a resilient, high coefficient of friction material such as neoprene, white rubber, non-marking rubber, or like materials.

13. An apparatus as defined in claim 1, wherein said motor and said drive belt pulley do not move linearly as said carriage member moves in a linear fashion toward and away from the glass container in the inspection station.

14. An apparatus as defined in claim 1, additionally comprising:

at least one idler pulley mounted on said carriage member near said proximal end thereof upon which said ware rotate belt is mounted, wherein said drive belt pulley is located closer to said distal end of said carriage member than is said at least one idler pulley; and wherein whenever the glass container in the inspection station has not yet been spun up to full rotation speed by said ware rotate belt, said motor will operate said drive belt pulley to increase the tension in the portion of said ware rotate belt extending from said ware rotate wheel around said at least one idler pulley to said drive belt pulley, thereby urging said carriage member in a distal direction toward the glass container in the inspection station.

15. An apparatus as defined in claim 1, additionally comprising:

a tensioner member including an idler pulley that is adjustable to adjust the tension on said drive ware rotate belt.

16. An apparatus as defined in claim 1, wherein said drive belt pulley, said ware rotate belt, and said ware rotate wheel are all located in the same horizontal plane.

17. An apparatus as defined in claim 1, additionally comprising:

at least one idler pulley mounted in at least one of said base member and said carriage member;

wherein said ware rotate wheel, said drive belt pulley, and said at least one idler pulley and the path of said ware rotate belt are respectively arranged and configured so that whenever the glass container in the inspection station has not yet been spun up to full rotation speed by said ware rotate belt, said motor will operate said drive belt pulley to increase the tension in the portion of said ware rotate belt extending from said ware rotate wheel around said at least one idler pulley to said drive belt pulley, thereby urging said carriage member in a distal direction toward the glass container in the inspection station.

18. An apparatus for rotating glass containers that are sequentially indexed into and out of an inspection station supporting the glass container to be inspected in vertical fashion on a surface, the inspection station having rollers for supporting a glass container in the inspection station for rotation on a side opposite a side of the glass container to be engaged by said apparatus for rotating glass containers, said apparatus for rotating glass containers comprising:
- a base member for installation in an adjustably fixed position with respect to the inspection station on the side of the glass container in the inspection station opposite the side of the glass container supported by the roller;
- a pair of guides coupled to the base member;
- a carriage member slidingly mounted between the pair of guides coupled to said base member in a linearly moveable fashion, relative to the base member, toward and away from the glass container in the inspection station, said carriage member having opposite proximal and distal ends, said distal end being closest to the inspection station and said proximal end being furthest from the inspection station;
- one or more biasing springs that apply a force to said carriage to urge the distal end of said carriage toward the glass container in the inspection station;
- a ware rotate wheel that is rotatably mounted on said carriage member near said distal end thereof such that a portion of said ware rotate wheel extends outwardly proximate said distal end of said carriage member;
- a motor having a drive belt pulley driven by said motor, said motor and drive belt pulley do not move linearly as said carriage member moves;
- at least one idler pulley mounted on said carriage member near said proximal end thereof; and
- a ware rotate belt mounted on said drive belt pulley, said ware rotate wheel, and said at least one idler pulley, said motor thereby driving both said ware rotate belt and said ware rotate wheel;
- wherein a portion of said ware rotate belt is located upon the portion of said ware rotate wheel that extends outwardly proximate said distal end of said carriage member, said ware rotate belt contacting the side of the glass container in the inspection station opposite the side of the glass container supported by the rollers to rotate the glass container; and
- wherein said ware rotate wheel, said drive belt pulley, and said at least one idler pulley and the path of said ware rotate belt are respectively arranged and configured so that whenever the glass container in the inspection station has not yet been spun up to full rotation speed by said ware rotate belt, said motor will operate said drive belt pulley to increase the tension in the portion of said ware rotate belt extending from said ware rotate wheel around said at least one idler pulley to said drive belt pulley, thereby urging said whole carriage member in a distal direction toward the glass container in the inspection station.

19. An apparatus for rotating glass containers in an inspection station having rollers for supporting a glass container for rotation on a side opposite a side of the glass container to be engaged by said apparatus, said apparatus comprising:
- a base member for installation in a fixed position with respect to the inspection station on the side of the glass container in the inspection station opposite the side of the glass container supported by the rollers;
- a pair of guides coupled to the base member;
- a carriage member slidingly mounted between the pair of guides coupled to said base member in moveable fashion, relative to the base member, toward and away from the glass container in the inspection station, said carriage member having opposite proximal and distal ends;
- a ware rotate wheel that is rotatably mounted on said carriage member near an end thereof closest to the inspection station;
- a motor having a drive belt pulley driven by said motor; and
- a ware rotate belt mounted on said drive belt pulley and said ware rotate wheel, said motor thereby driving both said ware rotate belt and said ware rotate wheel;
- wherein a portion of said ware rotate belt located upon a portion of said ware rotate wheel contacts the side of the glass container in the inspection station to rotate the glass container.

20. A method of rotating glass containers that are sequentially indexed into and out of an inspection station supporting a glass container to be inspected in vertical fashion on a surface, the inspection station having rollers for supporting the glass container for rotation on a side opposite a side of the glass container to be engaged by said apparatus for rotating glass containers, said method for rotating glass containers comprising:
- installing a base member in an adjustably fixed position with respect to the inspection station on the side of the glass container in the inspection station opposite the side of the glass container supported by the rollers;
- mounting a carriage member between a pair of guides on said base member in a slidingly, linearly moveable fashion, relative to the base member, toward and away from the glass container in the inspection station, said carriage member having opposite proximal and distal ends, said distal end being closest to the inspection station and said proximal end being furthest from the inspection station;
- rotatably mounting a ware rotate wheel on said carriage member near said distal end thereof such that a portion of said ware rotate wheel extends outwardly proximate said distal end of said carriage member;
- driving a drive belt pulley with a motor; and
- mounting a ware rotate belt on said drive belt pulley and said ware rotate wheel, said motor thereby driving both said ware rotate belt and said ware rotate wheel with the ware rotate belt configured to pull the whole carriage member toward the glass container as belt tension increases;
- wherein a portion of said ware rotate belt is located upon the portion of said ware rotate wheel that extends outwardly proximate said distal end of said carriage member, said ware rotate belt contacting the side of the glass container in the inspection station opposite the side of the glass container supported by the rollers to rotate the glass container.

\* \* \* \* \*